(12) United States Patent
Dour et al.

(10) Patent No.: US 11,670,144 B2
(45) Date of Patent: Jun. 6, 2023

(54) USER INTERFACES FOR INDICATING DISTANCE

(71) Applicant: Apple Inc., Cupertino, CA (US)

(72) Inventors: Ryan N. Dour, San Francisco, CA (US); Robert Thomas Aloe, Campbell, CA (US); James Cartwright, Campbell, CA (US); Elizabeth Caroline Cranfill, San Francisco, CA (US); Giovanni Laviste Denina, Cupertino, CA (US); Christopher B. Fleizach, Gilroy, CA (US); Banafsheh Jalali, San Jose, CA (US); Chia Yang Lin, San Francisco, CA (US); Donald L. Marotta, Jr., Las Vegas, NV (US); Darren Christopher Minifie, Santa Cruz, CA (US); Grant Paul, San Francisco, CA (US); Per Haakan Linus Persson, Cupertino, CA (US); Antoine Tarault, Campbell, CA (US); Alexander Nicholas Walczak, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 109 days.

(21) Appl. No.: 17/398,617

(22) Filed: Aug. 10, 2021

(65) Prior Publication Data
US 2022/0084374 A1   Mar. 17, 2022

Related U.S. Application Data

(60) Provisional application No. 63/078,234, filed on Sep. 14, 2020.

(51) Int. Cl.
*G08B 7/06* (2006.01)
*G06T 11/00* (2006.01)
(Continued)

(52) U.S. Cl.
CPC ............. *G08B 7/06* (2013.01); *G06F 3/0484* (2013.01); *G06F 3/165* (2013.01); *G06T 11/00* (2013.01);
(Continued)

(58) Field of Classification Search
CPC ...... G08B 7/06; G08B 21/0476; G08B 21/02; G08B 21/22; G06F 3/0484; G06F 3/165;
(Continued)

(56) References Cited

U.S. PATENT DOCUMENTS 8,215,774 B2   7/2012   Korb et al.
9,197,275 B2 *  11/2015   Fathollahi ................. G06T 7/74
(Continued)

FOREIGN PATENT DOCUMENTS

CN        102573497 A      7/2012
CN        104094082 A     10/2014
(Continued)

OTHER PUBLICATIONS

Office Action received for Chinese Patent Application No. 202010125845.9, dated Oct. 21, 2021, 15 pages (6 pages of English Translation and 9 pages of Official Copy).
(Continued)

*Primary Examiner* — Curtis J King
(74) *Attorney, Agent, or Firm* — DLA Piper LLP (US)

(57) ABSTRACT

The present disclosure generally relates to providing indicators of distance. For example, display of a visual distance indicator that indicates the distance between a computer system and an entity is provided.

54 Claims, 16 Drawing Sheets

(51) Int. Cl.
| | |
|---|---|
| *G06F 3/0484* | (2022.01) |
| *G06F 3/16* | (2006.01) |
| *G08B 21/04* | (2006.01) |
| *H04N 23/63* | (2023.01) |
| G06T 7/50 | (2017.01) |
| G08B 21/02 | (2006.01) |

(52) U.S. Cl.
CPC ....... *G08B 21/0476* (2013.01); *H04N 23/631* (2023.01); *G06T 7/50* (2017.01); *G08B 21/02* (2013.01)

(58) Field of Classification Search
CPC ...... G06F 1/1686; G06F 3/0304; G06F 3/167; G06F 3/0481; G06F 3/011; G06T 11/00; G06T 7/50; H04N 23/631; H04N 23/62; G01B 11/026; G06Q 50/26; G16H 50/80; H04M 2250/52; H04M 1/72454
See application file for complete search history.

(56) References Cited

U.S. PATENT DOCUMENTS

| | | | |
|---|---|---|---|
| 10,599,920 B2* | 3/2020 | Mojaver | G06V 40/28 |
| 10,803,609 B2 | 10/2020 | Oka | |
| 2009/0138233 A1 | 5/2009 | Kludas et al. | |
| 2009/0293012 A1* | 11/2009 | Alter | G06T 15/10 |
| | | | 715/848 |
| 2010/0111370 A1 | 5/2010 | Black et al. | |
| 2010/0253907 A1 | 10/2010 | Korb et al. | |
| 2010/0321490 A1 | 12/2010 | Chen et al. | |
| 2012/0001938 A1 | 1/2012 | Sandberg | |
| 2012/0019674 A1 | 1/2012 | Ohnishi et al. | |
| 2012/0206597 A1 | 8/2012 | Komoto et al. | |
| 2013/0197793 A1 | 8/2013 | Vaddadi et al. | |
| 2013/0201210 A1 | 8/2013 | Vaddadi et al. | |
| 2013/0247117 A1 | 9/2013 | Yamada et al. | |
| 2013/0337789 A1 | 12/2013 | Johnson | |
| 2014/0132411 A1* | 5/2014 | Buchheim | G01S 5/0231 |
| | | | 340/8.1 |
| 2014/0232636 A1 | 8/2014 | Hara | |
| 2014/0267409 A1* | 9/2014 | Fein | G06T 11/00 |
| | | | 345/633 |
| 2014/0267410 A1* | 9/2014 | Fein | G06Q 30/0641 |
| | | | 345/633 |
| 2014/0267411 A1* | 9/2014 | Fein | G06F 16/29 |
| | | | 345/633 |
| 2014/0315603 A1* | 10/2014 | Fathollahi | A45C 11/00 |
| | | | 455/575.8 |
| 2015/0084755 A1 | 3/2015 | Chen et al. | |
| 2015/0094118 A1* | 4/2015 | Rodolico | G06V 40/20 |
| | | | 455/566 |
| 2016/0072541 A1* | 3/2016 | Fathollahi | G06T 7/74 |
| | | | 455/575.8 |
| 2016/0179454 A1* | 6/2016 | Liu | G06F 3/04886 |
| | | | 715/747 |
| 2016/0189386 A1 | 6/2016 | Michaelraj et al. | |
| 2016/0203641 A1 | 7/2016 | Bostick et al. | |
| 2016/0330379 A1 | 11/2016 | Lee et al. | |
| 2017/0034431 A1 | 2/2017 | Malgimani et al. | |
| 2017/0148188 A1* | 5/2017 | Fathollahi | H04M 1/0264 |
| 2017/0161561 A1 | 6/2017 | Marty et al. | |
| 2018/0075301 A1* | 3/2018 | Everhart | G06V 20/20 |
| 2018/0211411 A1* | 7/2018 | Fathollahi | H04M 1/185 |
| 2019/0096135 A1 | 3/2019 | Dal Mutto et al. | |
| 2019/0297313 A1 | 9/2019 | Nolan et al. | |
| 2020/0250846 A1 | 8/2020 | Oka | |
| 2020/0279386 A1 | 9/2020 | Da Veiga | |
| 2021/0158621 A1* | 5/2021 | Shatkina | G06T 19/006 |
| 2021/0241477 A1 | 8/2021 | Da Veiga | |
| 2022/0189075 A1* | 6/2022 | Lynch | G06F 3/04883 |

FOREIGN PATENT DOCUMENTS

| | | |
|---|---|---|
| CN | 104094083 A | 10/2014 |
| CN | 105745122 A | 7/2016 |
| JP | 2018-40789 A | 3/2018 |
| WO | 2015/039776 A1 | 3/2015 |
| WO | 2017/007643 A1 | 1/2017 |
| WO | 2019/245550 A1 | 12/2019 |

OTHER PUBLICATIONS

Notice of Allowance received for U.S. Appl. No. 17/234,640, dated Nov. 9, 2022, 10 pages.
Non-Final Office Action received for U.S. Appl. No. 17/234,640, dated Jul. 1, 2022, 17 pages.
Office Action received for Chinese Patent Application No. 202010125845.9, dated Jun. 6, 2022, 10 pages (5 pages of English Translation and 5 pages of Official Copy).
Applicant-Initiated Interview Summary received for U.S. Appl. No. 16/801,548, dated Nov. 2, 2020, 3 pages.
Apple Support, "Use the Measure app on your iPhone, iPad, or iPod touch", Online Available at: https://support.apple.com/en-us/HT208924, Apr. 23, 2020, 5 pages.
Caramba Apps, "EasyMeasure—Measure with your Camera!", Online available at: https://www.caramba-apps.com/easymeasure/, retrieved on: Sep. 14, 2020, 5 pages.
Ghazouani, Hamza, "A beautiful radar view to show nearby items with ripple animation", Online Available at: https://iosexample.com/a-beautiful-radar-view-to-show-nearby-items-with-ripple-animation/, Dec. 3, 2018, 12 pages.
Non-Final Office Action received for U.S. Appl. No. 16/801,548 dated Sep. 25, 2020, 13 pages.
Notice of Allowance received for U.S. Appl. No. 16/801,548, dated Dec. 9, 2020, 10 pages.
International Search Report and Written Opinion received for PCT Patent Application No. PCT/US2021/048421, dated Dec. 8, 2021, 15 pages.
Prajanified, "App which will help you maintain social distancing! How to use Sodar app", Online Available at: https://www.youtube.com/watch?v=kmpyc8SNeX4, Jun. 9, 2020, 3 pages.
Notice of Allowance received for Chinese Patent Application No. 202010125845.9, dated Oct. 8, 2022, 4 pages (1 page of English Translation and 3 pages of Official Copy).
Notice of Allowance received for U.S. Appl. No. 17/234,640, dated Jan. 6, 2023, 2 pages.
International Preliminary Report on Patentability received for PCT Patent Application No. PCT/US2021/048421, dated Mar. 23, 2023, 11 pages.

* cited by examiner

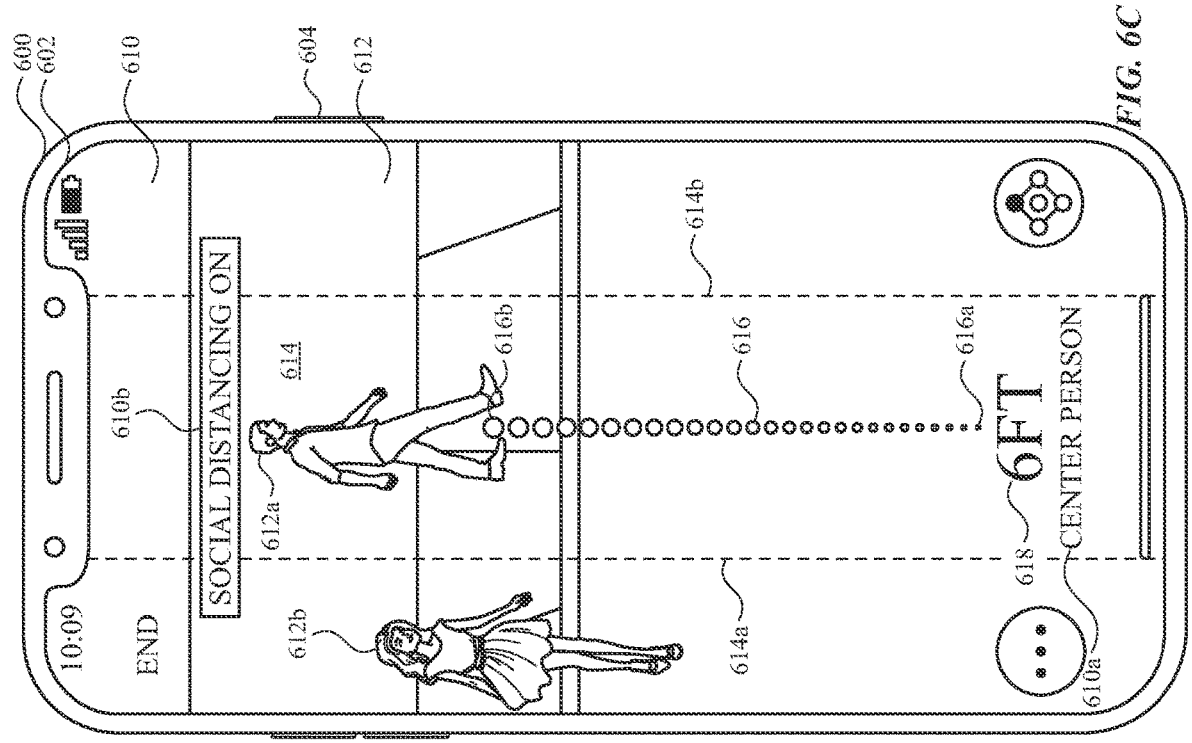
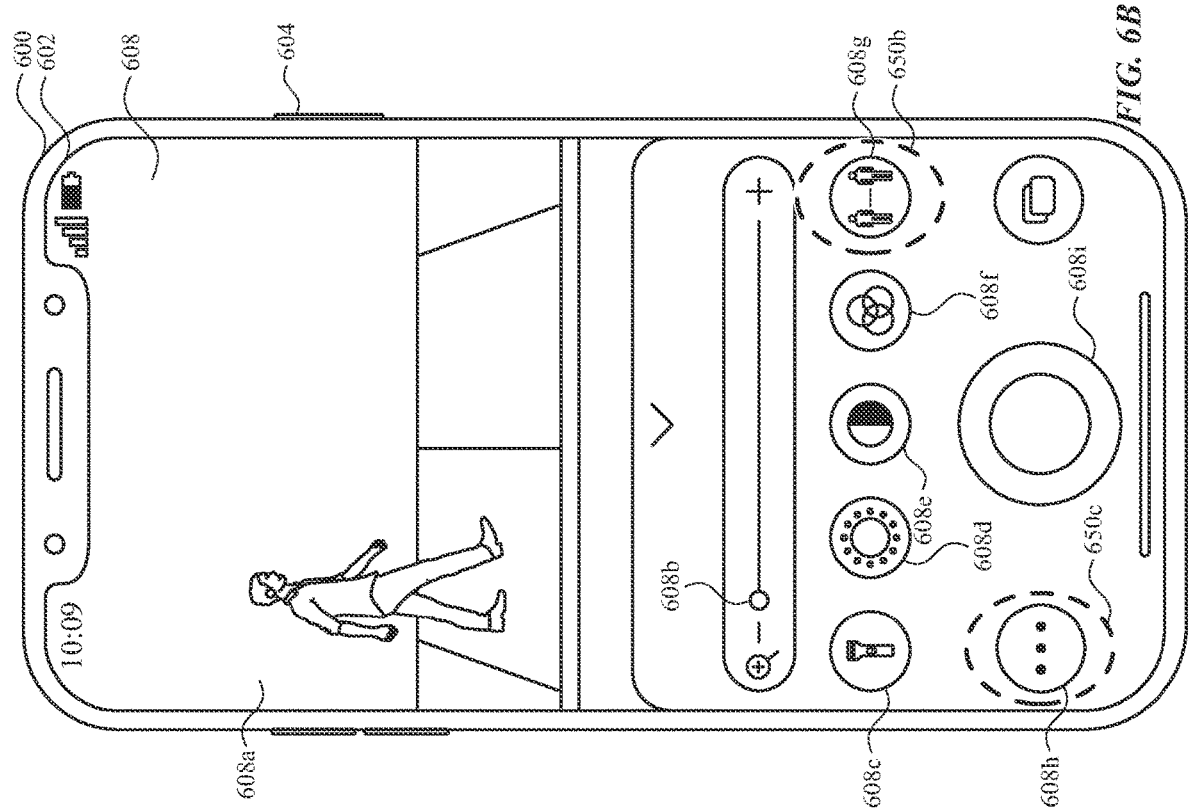

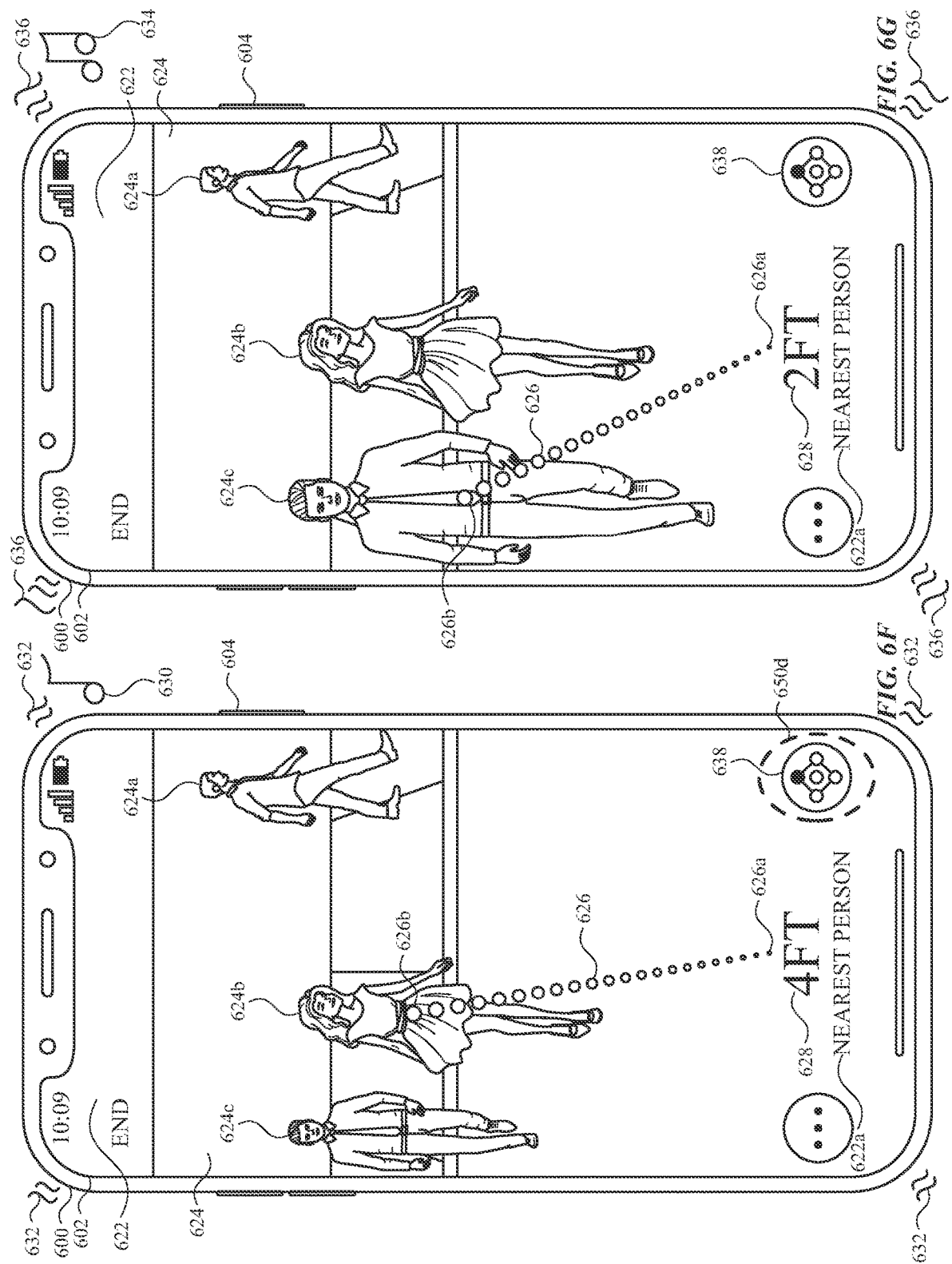

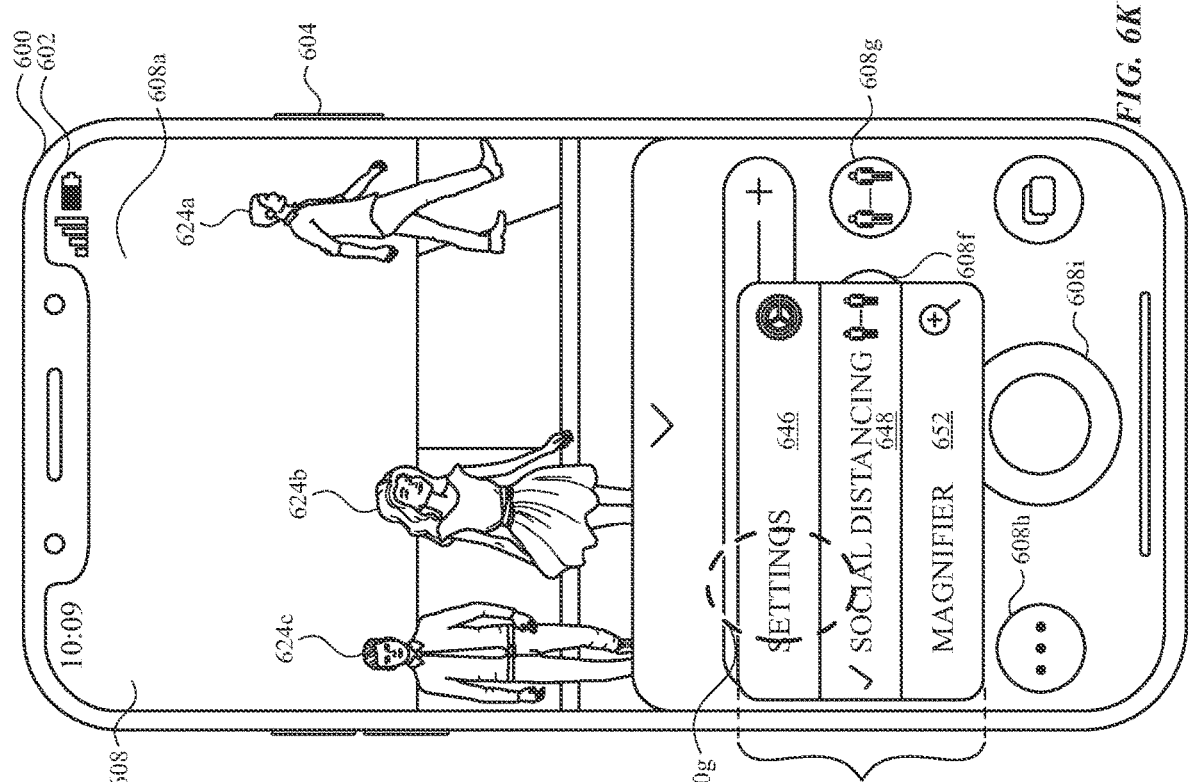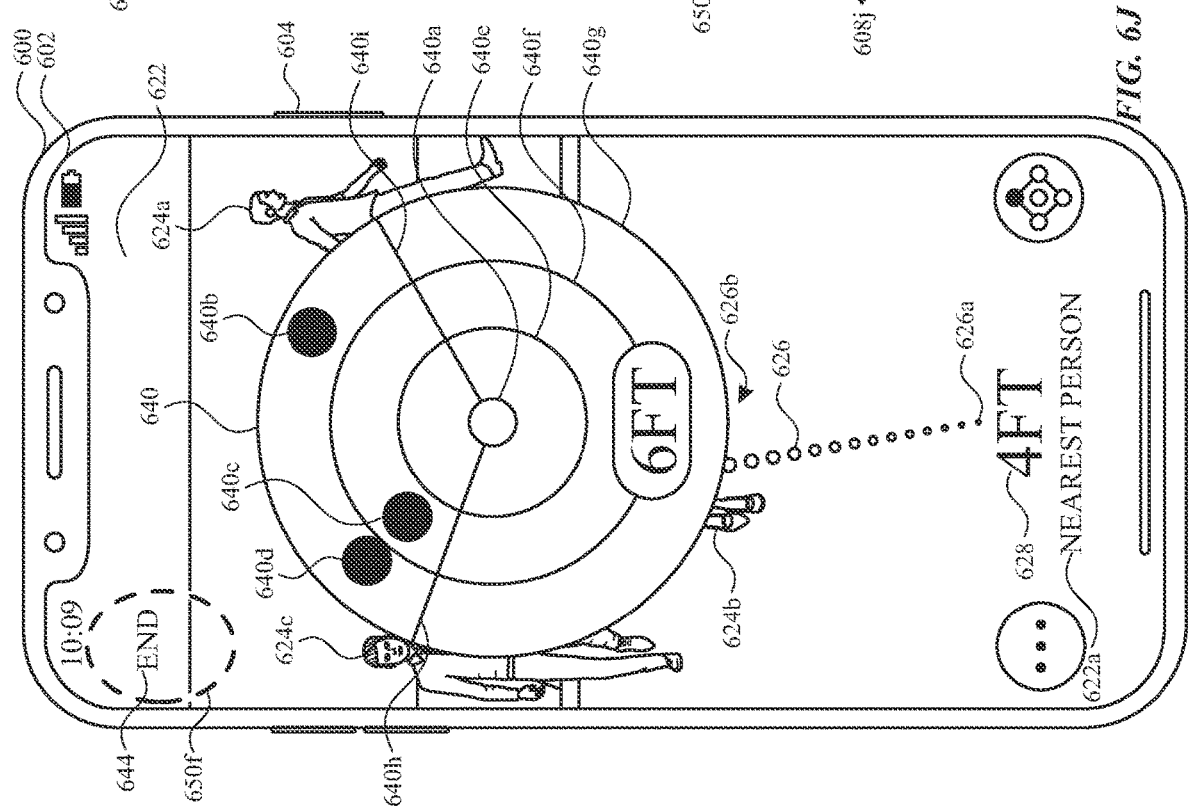

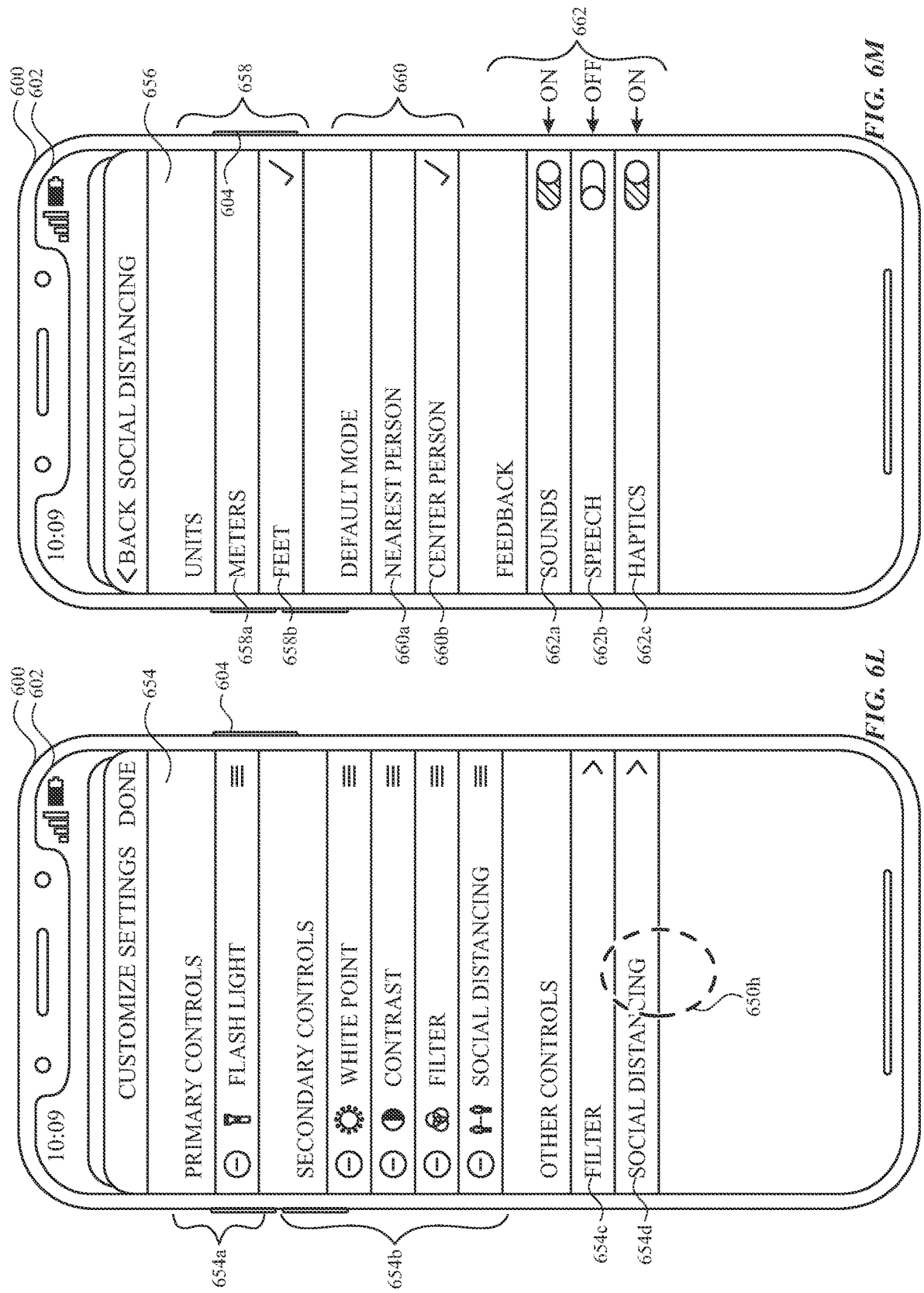

700 

702
Display a visual representation of a field of view of one or more cameras.

704
In accordance with a determination that an entity meets a set of detection criteria, the set of detection criteria including a first criterion that is met when the entity is detected within the field of view of the one or more cameras:

706
Provide, concurrently with the visual representation of the field of view that includes the entity, one or more indicators of distance between the computer system and the entity, wherein providing the one or more indicators of distance includes displaying a visual distance indicator that indicates the distance between the computer system and the entity.

708
In accordance with a failure to determine that an entity meets the set of detection criteria:

710
Forgo providing the one or more indicators of a distance between the computer system and the entity.

*FIG. 7*

USER INTERFACES FOR INDICATING DISTANCE

CROSS-REFERENCE TO RELATED APPLICATIONS

This application claims benefit to U.S. Provisional Application No. 63/078,234, filed Sep. 14, 2020, entitled "USER INTERFACES FOR INDICATING DISTANCE," the entire contents of which are hereby incorporated by reference.

FIELD

The present disclosure relates generally to computer user interfaces, and more specifically to techniques for providing an indication of distance to an entity.

BACKGROUND

Computer systems can include features for identifying entities using, for example, a camera of the computer systems. Computer systems can also determine a distance between two stationary points within a field of view of the camera.

BRIEF SUMMARY

Some techniques for providing a distance using electronic devices, however, are generally cumbersome and inefficient. For example, some existing techniques provide distance between two or more points within a field of view of an electronic device, but do not provide an indication of distance between a point within the field of view and the electronic device itself. In addition, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for providing an indication of distance to an entity. Such methods and interfaces optionally complement or replace other methods for providing an indication of distance to an entity. Such methods and interfaces reduce the cognitive burden on a user and produce a more efficient human-machine interface. For battery-operated computing devices, such methods and interfaces conserve power and increase the time between battery charges.

In accordance with some embodiments, a method performed at a computer system that is in communication with one or more cameras and a display generation component is described. The method comprises: displaying, via the display generation component, a visual representation of a field of view of the one or more cameras; in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes: displaying, via the display generation component, a visual distance indicator that indicates the distance between the computer system and the entity; and in accordance with a failure to determine that an entity meets the set of detection criteria, forgoing providing the one or more indicators of a distance between the computer system and the entity.

In accordance with some embodiments, a non-transitory computer-readable storage medium is described. The non-transitory computer-readable storage medium stores one or more programs configured to be executed by one or more processors of a computer system that is in communication with one or more cameras and a display generation component, the one or more programs including instructions for: displaying, via the display generation component, a visual representation of a field of view of the one or more cameras; in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes: displaying, via the display generation component, a visual distance indicator that indicates the distance between the computer system and the entity; and in accordance with a failure to determine that an entity meets the set of detection criteria, forgoing providing the one or more indicators of a distance between the computer system and the entity.

In accordance with some embodiments, a transitory computer-readable storage medium is described. The transitory computer-readable storage medium stores one or more programs configured to be executed by one or more processors of a computer system that is in communication with one or more cameras and a display generation component, the one or more programs including instructions for: displaying, via the display generation component, a visual representation of a field of view of the one or more cameras; in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes: displaying, via the display generation component, a visual distance indicator that indicates the distance between the computer system and the entity; and in accordance with a failure to determine that an entity meets the set of detection criteria, forgoing providing the one or more indicators of a distance between the computer system and the entity.

In accordance with some embodiments, a computer system is described. The computer system comprises: one or more cameras; a display generation component; one or more processors; and memory storing one or more programs configured to be executed by the one or more processors, the one or more programs including instructions for: displaying, via the display generation component, a visual representation of a field of view of the one or more cameras; in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes: displaying, via the display generation component, a visual distance indicator that indicates the distance between the computer system and the entity; and in accordance with a failure to determine that an entity meets the set of detection criteria, forgoing providing the one or more indicators of a distance between the computer system and the entity.

In accordance with some embodiments, a computer system is described. The computer system comprises: one or more cameras; a display generation component; means for displaying, via the display generation component, a visual representation of a field of view of the one or more cameras; means, in accordance with a determination that an entity meets a set of detection criteria, the set of detection criteria including a first criterion that is met when the entity is detected within the field of view of the one or more cameras, for providing, concurrently with the visual representation of the field of view that includes the entity, one or more indicators of distance between the computer system and the entity, wherein providing the one or more indicators of distance includes: displaying, via the display generation component, a visual distance indicator that indicates the distance between the computer system and the entity; and means, in accordance with a failure to determine that an entity meets the set of detection criteria, for forgoing providing the one or more indicators of a distance between the computer system and the entity.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for providing an indication of distance to an entity, thereby increasing the effectiveness, efficiency, and user satisfaction with such devices. Such methods and interfaces may complement or replace other methods for providing an indication of distance to an entity.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 6A-6M illustrate exemplary user interfaces for providing an indication of distance to an entity in accordance with some embodiments.

FIG. 7 is a flow diagram illustrating a method for providing an indication of distance to an entity in accordance with some embodiments.

DESCRIPTION OF EMBODIMENTS

Figure 1A:
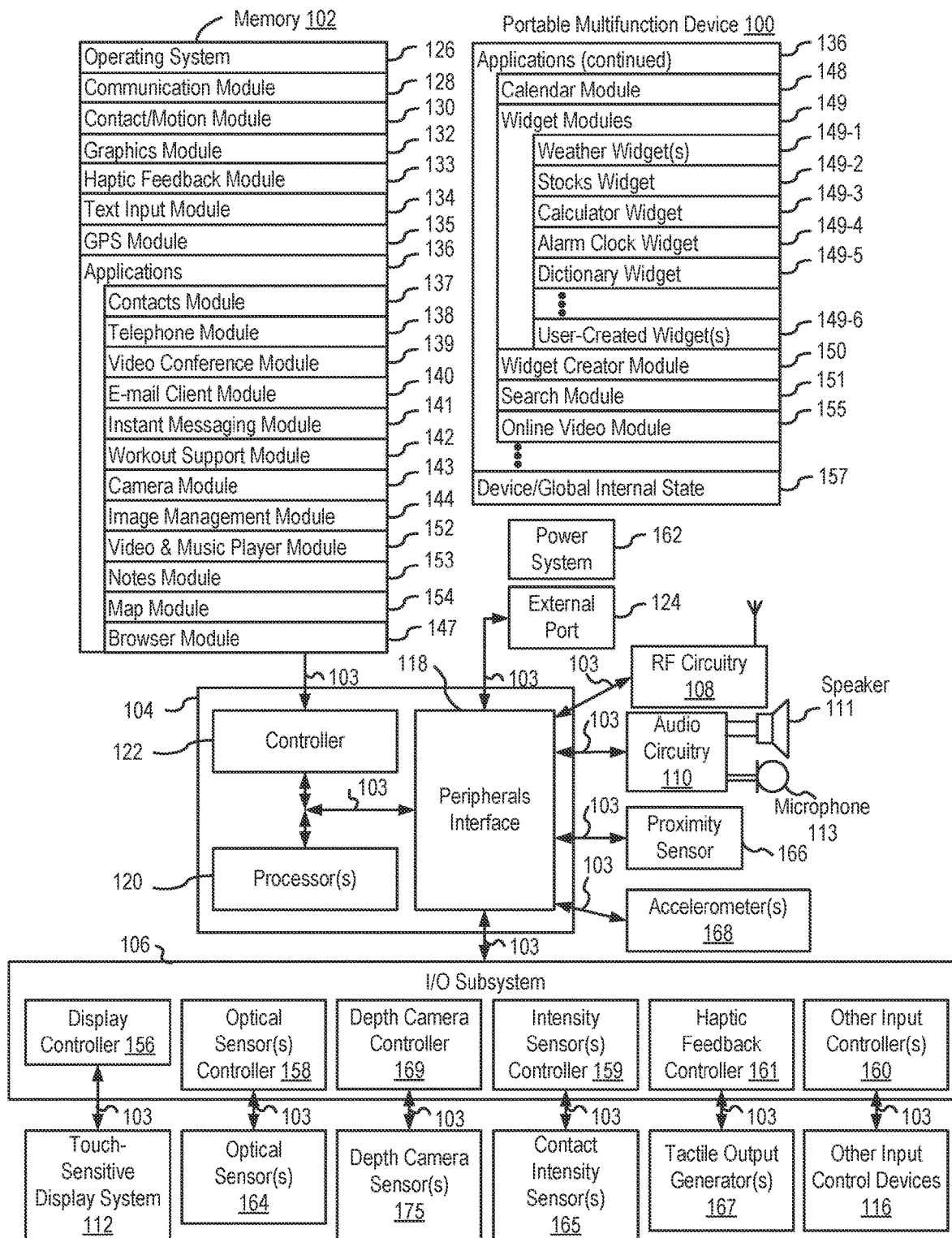
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for providing an indication of distance to an entity. For example, a user that is vision impaired can have difficulty estimating a distance between the user and another person or object in front of the user. Displaying a user interface on an electronic device that provides an indication of distance to an entity enable the user to quickly and accurately determine how far another person or object is to the electronic device, and thus, how far another person or object is to the user holding the electronic device. Such techniques can reduce the cognitive burden on a user who request a determination of distance to an entity, thereby enhancing productivity. Further, such techniques can reduce processor and battery power otherwise wasted on redundant user inputs.

Below, FIGS. 1A-1B, 2, 3, 4A-4B, and 5A-5B provide a description of exemplary devices for performing the techniques for providing an indication of distance to an entity. FIGS. 6A-6M illustrate exemplary user interfaces for providing an indication of distance to an entity. FIG. 7 is a flow diagram illustrating methods of providing an indication of distance to an entity in accordance with some embodiments. The user interfaces in FIGS. 6A-6M are used to illustrate the processes described below, including the processes in FIG. 7.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

In some embodiments, a depth map (e.g., depth map image) contains information (e.g., values) that relates to the distance of objects in a scene from a viewpoint (e.g., a camera, an optical sensor, a depth camera sensor). In one embodiment of a depth map, each depth pixel defines the position in the viewpoint's Z-axis where its corresponding two-dimensional pixel is located. In some embodiments, a depth map is composed of pixels wherein each pixel is defined by a value (e.g., 0-255). For example, the "0" value represents pixels that are located at the most distant place in a "three dimensional" scene and the "255" value represents pixels that are located closest to a viewpoint (e.g., a camera, an optical sensor, a depth camera sensor) in the "three dimensional" scene. In other embodiments, a depth map represents the distance between an object in a scene and the plane of the viewpoint. In some embodiments, the depth map includes information about the relative depth of various features of an object of interest in view of the depth camera (e.g., the relative depth of eyes, nose, mouth, ears of a user's face). In some embodiments, the depth map includes information that enables the device to determine contours of the object of interest in a z direction.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
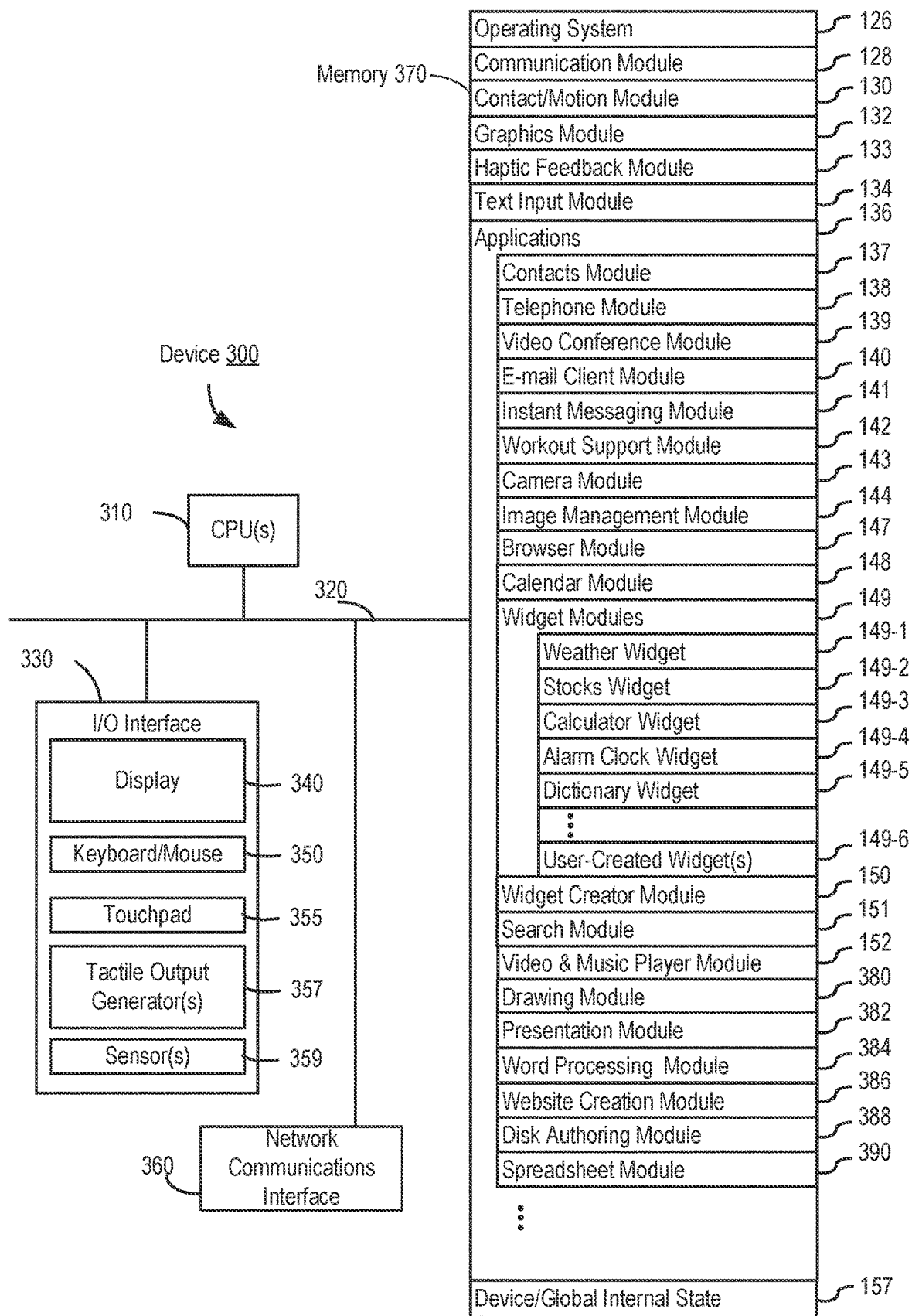
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module 130 (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
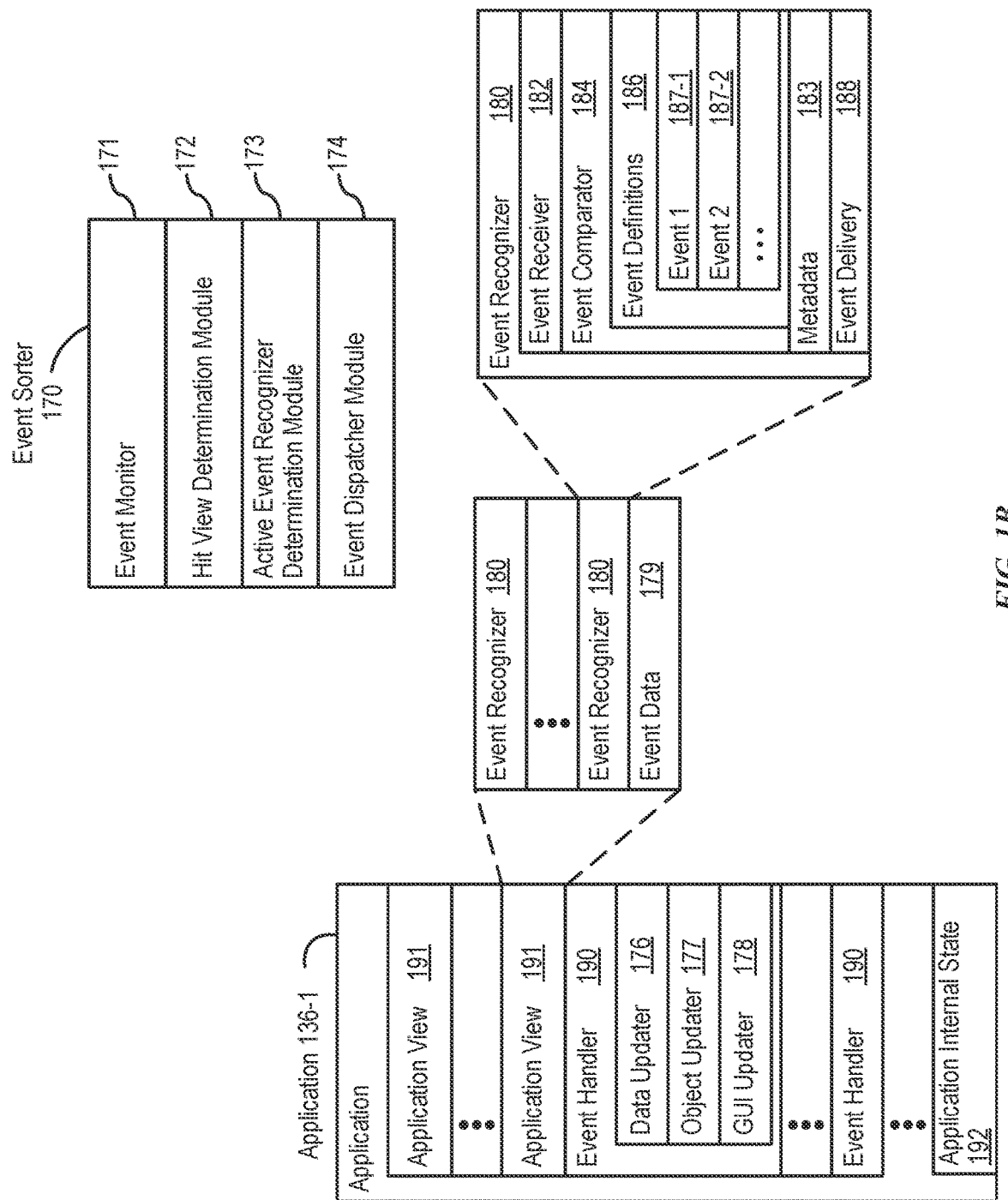
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
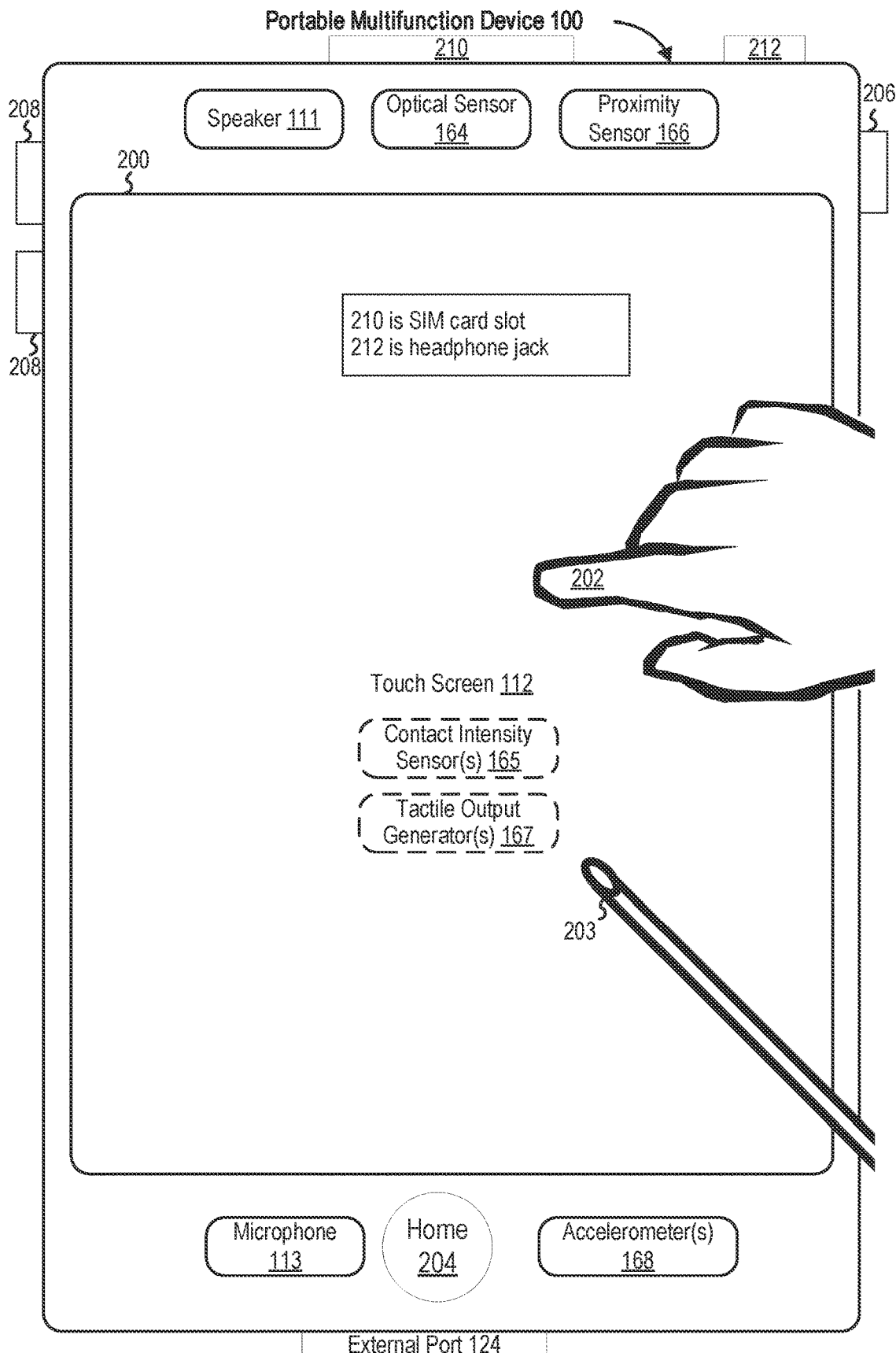
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
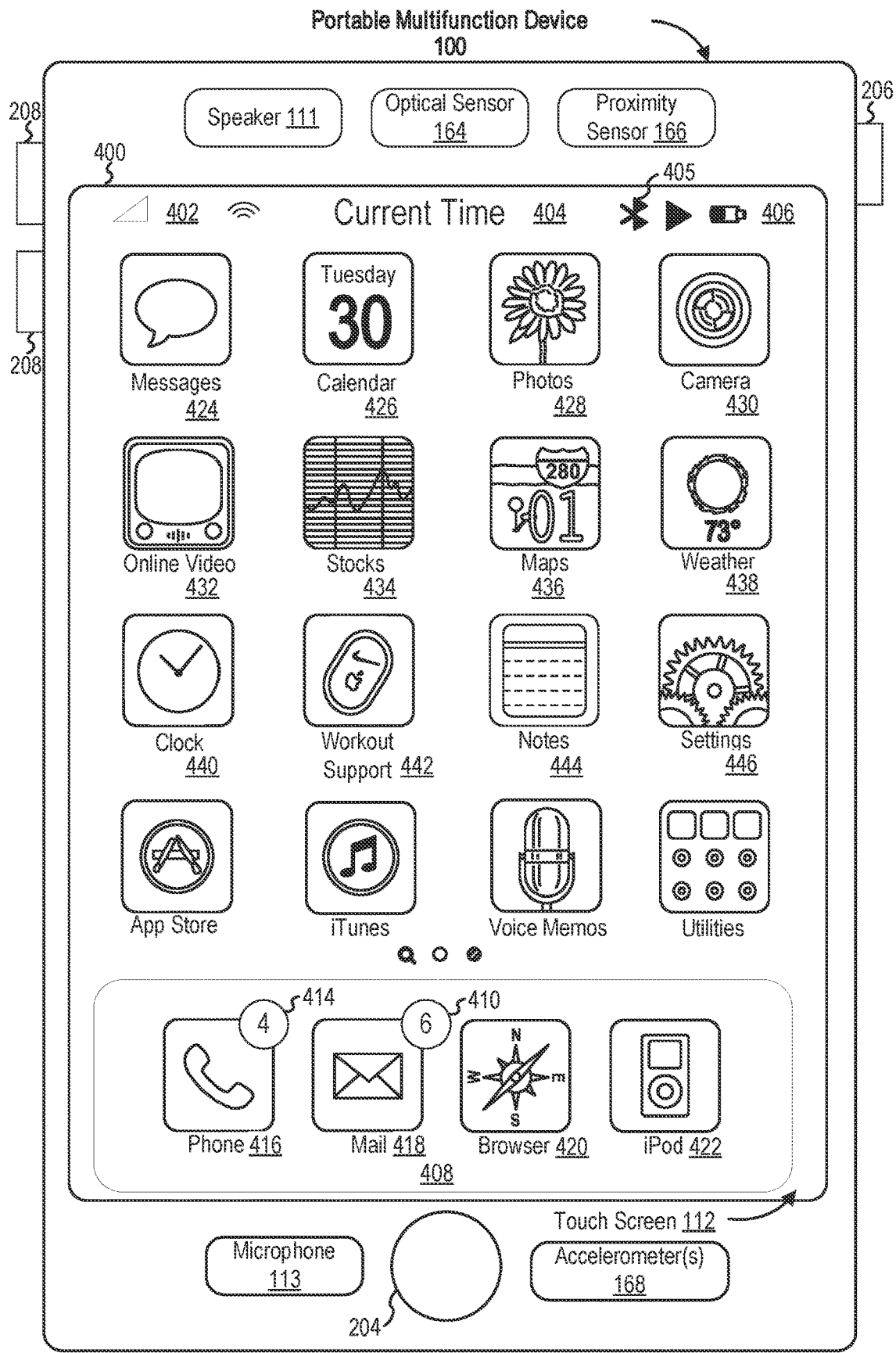
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
- Icon 416 for telephone module 138, labeled "Phone," which optionally includes an indicator 414 of the number of missed calls or voicemail messages;
- Icon 418 for e-mail client module 140, labeled "Mail," which optionally includes an indicator 410 of the number of unread e-mails;
- Icon 420 for browser module 147, labeled "Browser;" and
- Icon 422 for video and music player module 152, also referred to as iPod (trademark of Apple Inc.) module 152, labeled "iPod;" and Icons for other applications, such as:
- Icon 424 for IM module 141, labeled "Messages;"
- Icon 426 for calendar module 148, labeled "Calendar;"
- Icon 428 for image management module 144, labeled "Photos;"
- Icon 430 for camera module 143, labeled "Camera;"
- Icon 432 for online video module 155, labeled "Online Video;"
- Icon 434 for stocks widget 149-2, labeled "Stocks;"
- Icon 436 for map module 154, labeled "Maps;"
- Icon 438 for weather widget 149-1, labeled "Weather;"
- Icon 440 for alarm clock widget 149-4, labeled "Clock;"
- Icon 442 for workout support module 142, labeled "Workout Support;"
- Icon 444 for notes module 153, labeled "Notes;" and
- Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
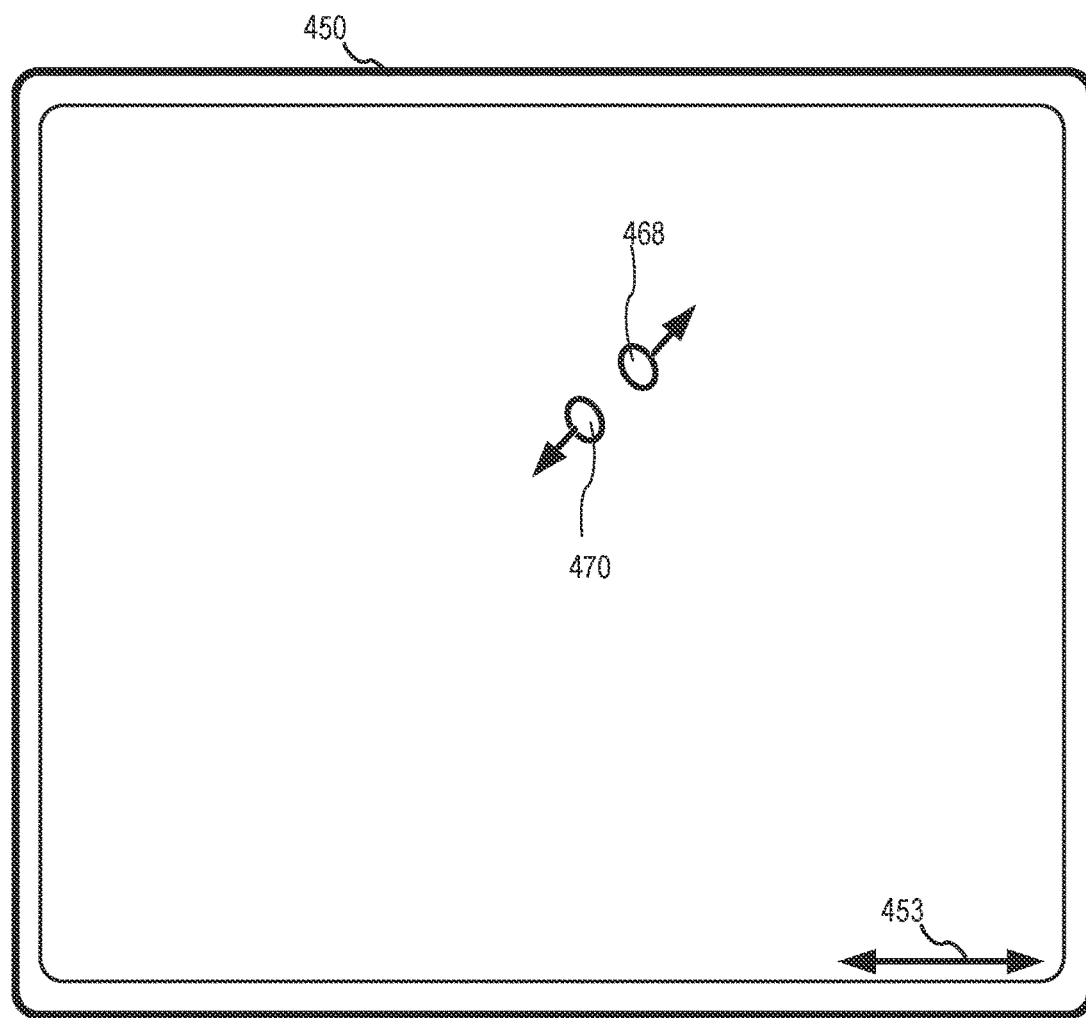
FIG. 4B illustrates an exemplary user interface for a multifunction device with a touch-sensitive surface that is separate from the display in accordance with some embodiments.
Figure 4B:
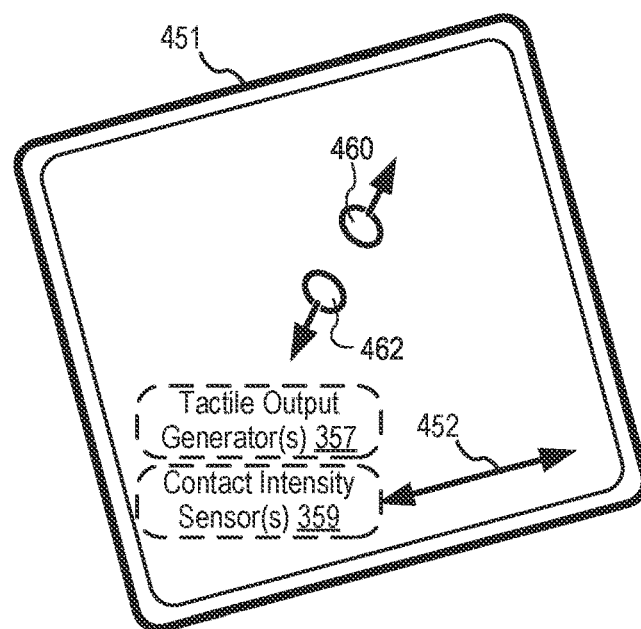

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
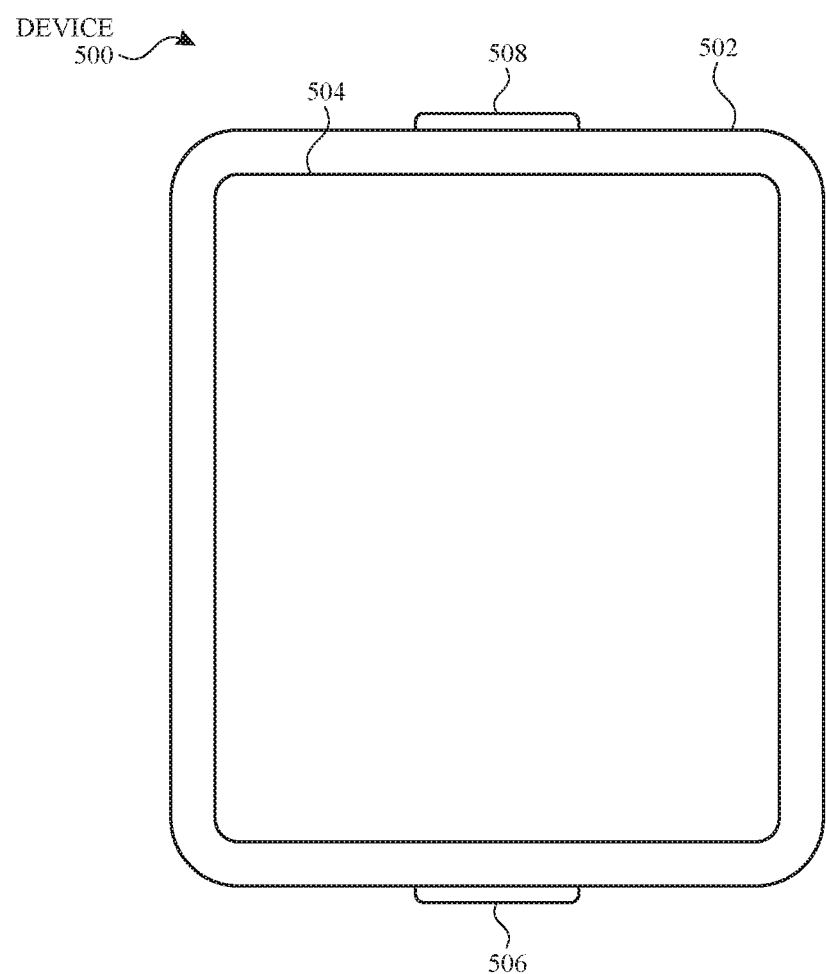
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
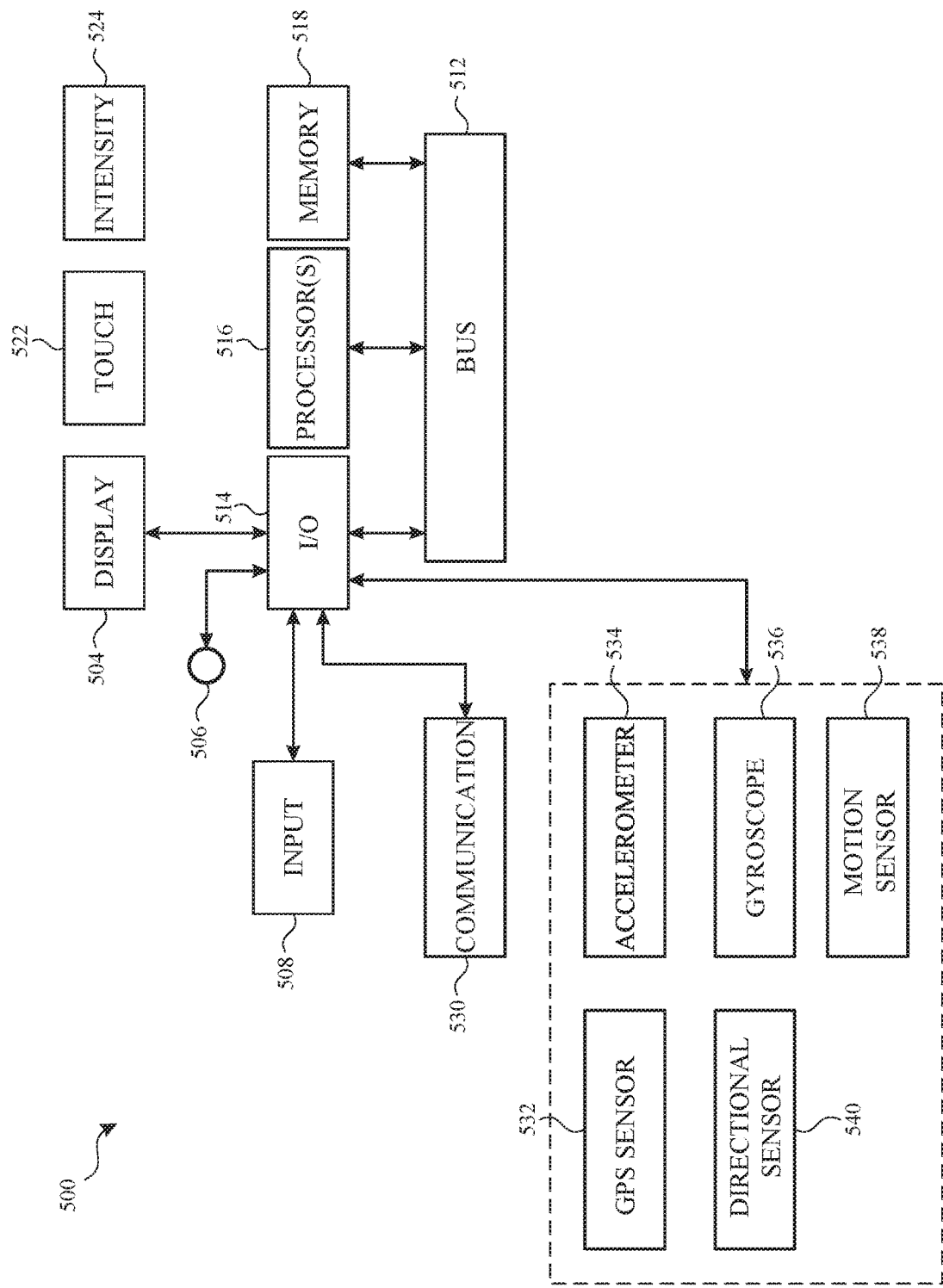
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including process 700 (FIG. 7). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

Tactile output patterns may have a corresponding characteristic frequency that affects the "pitch" of a haptic sensation that is felt by a user from a tactile output with that characteristic frequency. For a continuous tactile output, the characteristic frequency represents the number of cycles that are completed within a given period of time (e.g., cycles per second) by the moveable mass of the tactile output generator. For a discrete tactile output, a discrete output signal (e.g., with 0.5, 1, or 2 cycles) is generated, and the characteristic frequency value specifies how fast the moveable mass needs to move to generate a tactile output with that characteristic frequency.

Tactile output patterns may have a characteristic amplitude that affects the amount of energy that is contained in a tactile signal, or a "strength" of a haptic sensation that may be felt by a user through a tactile output with that characteristic amplitude. In some embodiments, the characteristic amplitude of a tactile output pattern refers to an absolute or normalized value that represents the maximum displacement of the moveable mass from a neutral position when generating the tactile output. In some embodiments, the characteristic amplitude of a tactile output pattern is adjustable, e.g., by a fixed or dynamically determined gain factor (e.g., a value between 0 and 1), in accordance with various conditions (e.g., customized based on user interface contexts and behaviors) and/or preconfigured metrics (e.g., input-based metrics, and/or user-interface-based metrics). In some embodiments, the characteristic amplitude of a tactile output pattern may be modulated by an "envelope" and the peaks of adjacent cycles may have different amplitudes, where one of the waveforms shown above is further modified by multiplication by an envelope parameter that changes over time (e.g., from 0 to 1) to gradually adjust amplitude of portions of the tactile output over time as the tactile output is being generated.

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6M illustrate exemplary user interfaces for providing an indication of distance to an entity, in accordance with some embodiments. The user interfaces in these figures are used to illustrate the processes described below, including the processes in FIG. 7.

Figure 6A:
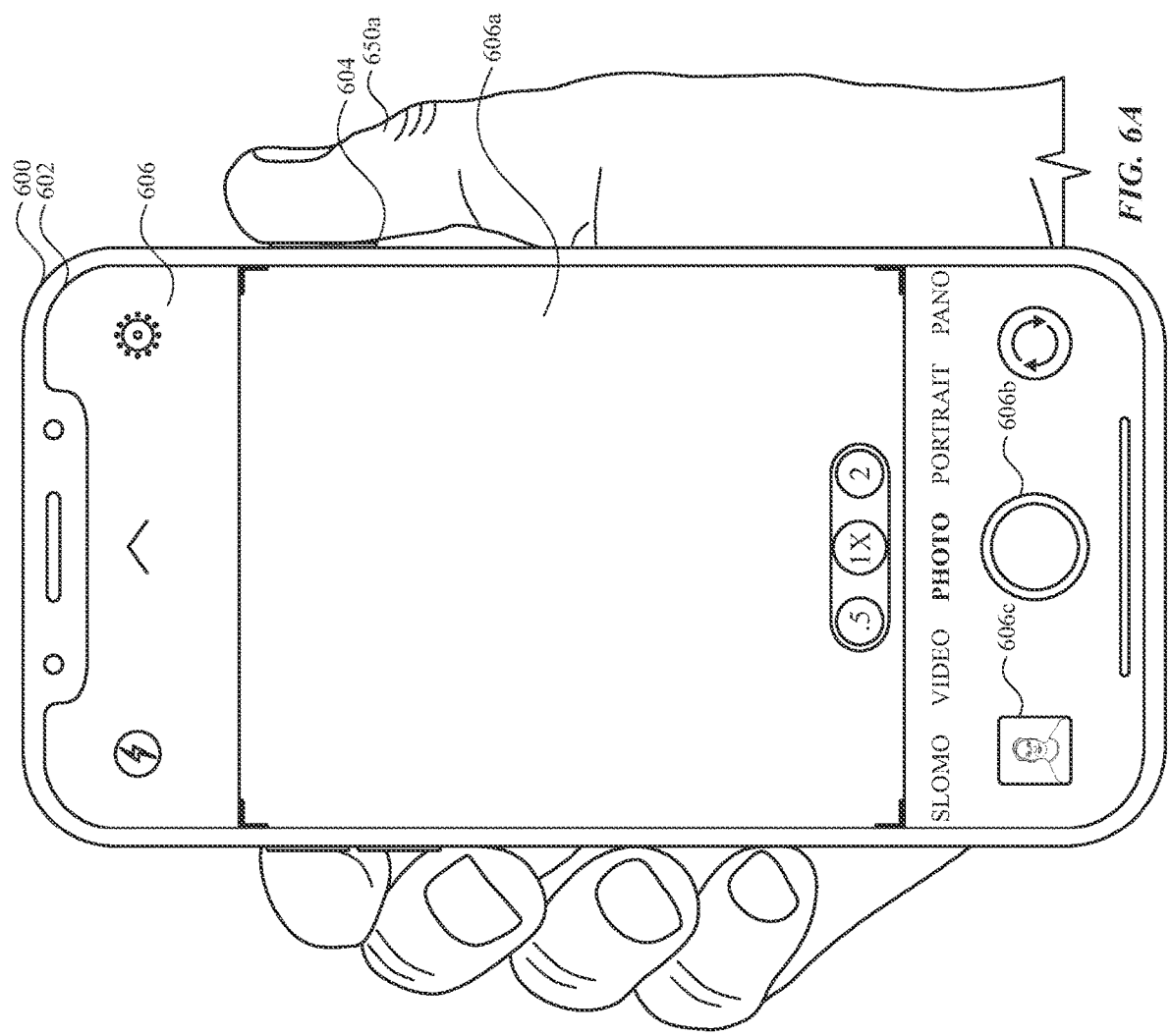

FIG. 6A illustrates electronic device 600 having a display 602 and side button 604. At FIG. 6A, electronic device 600 displays user interface 606 on display 602, where user interface 606 corresponds to a camera application that enables a user to capture images using a camera (e.g., of one or more cameras) of electronic device 600. For instance, user interface 606 includes a field of view representation 606a that includes a visual representation of an area surrounding electronic device 600 and that is within a field of view of the camera. User interface 606 also includes a capture user interface object 606b. In response to detecting user input corresponding to capture user interface object 606b, electronic device 600 causes an image to be captured that is within the field of view of the camera. Additionally, user interface 606 includes image library user interface object 606c. In response to detecting user input corresponding to selection of image library user interface object 606c, electronic device 600 displays an image library (e.g., an image library user interface) that includes images captured by electronic device 600.

At FIG. 6A, electronic device 600 detects user input 650a (e.g., a multi-tap or multi-press gesture, such as three successive taps or presses) on side button 604. In response to detecting user input 650a, electronic device 600 displays user interface 608 corresponding to a magnification application, as shown at FIG. 6B. For example, the magnification application enables a user to use device 600 to magnify (e.g., zoom) a representation of an area surrounding electronic device 600 that is within the field of view of the camera. In some embodiments, in response to detecting user input 650a while displaying user interface 606, electronic device displays user interface 608. In some embodiments, in response to detecting user input 650a, electronic device 600 displays user interface 608 independent of the user interface being displayed (e.g., a user interface other than 606).

At FIG. 6B, user interface 608 includes field of view representation 608a that includes a visual representation of an area surrounding electronic device 600 and that is within the field of view of the camera. User interface 608 also includes magnifier user interface object 608b, flash user interface object 608c, brightness user interface object 608d, contrast user interface object 608e, color user interface object 608f, distancing user interface object 608g, settings user interface object 608h, and capture user interface object 608i. In response to detecting user input (e.g., a swipe gesture and/or a tap gesture) on magnifier user interface object 608b, electronic device 600 is configured to zoom in or out the visual representation displayed at field of view representation 608a. In other words, in response to detecting a right swipe gesture on the magnifier user interface object 608b, electronic device 600 zooms in (e.g., magnifies) the visual representation displayed at the field of view representation 608a. In response to detecting a left swipe gesture on magnifier user interface object 608b, electronic device 600 zooms out (e.g., de-magnifies) the visual representation displayed at the field of view representation 608a. In some embodiments, distancing user interface object 608g is a toggle that causes electronic device 600 to activate a distancing feature in response to a first user input (e.g., when toggle is in an inactive position) and causes electronic device to deactivate the distancing feature in response to a second user input (e.g., when toggle is in an active position).

At FIG. 6B, electronic device 600 detects user input 650b (e.g., a tap gesture) on distancing user interface object 608g. In response to detecting user input 650b on distancing user interface object 608g, electronic device 600 displays distancing user interface 610, as shown at FIG. 6C. In some embodiments, electronic device 600 detects another user input, different from user input 650b to cause display of user interface 610. For example, electronic device 600 can be configured to cause display of user interface 610 in response to detecting a user-specific user input that is set by the user of electronic device 600. In some embodiments, the user-specific user input includes a gesture on display 602. In some embodiments, the user-specific user input includes a gesture on side button 604. Alternatively, electronic device can detect user input 650c (e.g., a tap gesture) on settings user interface object 608h. In response to detecting user input 650c on settings user interface object 608h, electronic device 600 displays user interface 608 with settings menu 608j, as shown at FIG. 6K.

At FIG. 6C, electronic device 600 displays distancing user interface 610 in response to detecting user input 650b. Distancing user interface 610 corresponds to a distancing feature of electronic device 600 that provides an indication of a distance between an entity (e.g., a person and/or an object) and electronic device 600 (and thus the user holding electronic device 600). The distancing feature of electronic device 600 enables a user to determine a distance between the user and an entity that is detected within a field of view (or a portion of a field of view) of the camera of electronic device 600. Thus, users that have a vision impairment may utilize electronic device 600 to determine how close an entity is to the device and user as the user holds electronic device 600.

At FIG. 6C, distancing user interface 610 includes a field of view representation 612, which displays a visual representation of a portion of an area surrounding electronic device 600 that is within a field of view of the camera (e.g., of one or more cameras) of electronic device 600. For example, the camera of electronic device 600 is configured to capture images of an area that is within the field of view of the camera (e.g., an area at which the camera is directed that is based on movement of electronic device 600 by the user). At FIG. 6C, field of view representation 612 includes first person 612a and second person 612b being within a field of view of the camera. At FIG. 6C, distancing user interface 610 corresponds to a first mode of the distancing feature of electronic device 600, as indicated by mode indicator 610a of distancing user interface 610. As discussed in detail below with reference to FIGS. 6E-6J, distancing user interface 622 corresponds to a second mode of the distancing feature of electronic device 600 as indicated by mode indicator 622a of distancing user interface 622.

In the first mode, distancing user interface 610 detects a closest entity (e.g., people and/or objects) to electronic device 600 that is positioned within center portion 614 of field of view representation 612. For instance, at FIG. 6C, center portion 614 of field of view representation 612 is represented by lines 614a and 614b along display 602 of electronic device 600. Lines 614a and 614b indicating center portion 614 are not displayed on distancing user interface 610, but rather are used for explanatory purposes to show the portions within field of view representation 612 that entities are detected when the distancing feature is active and in the first mode. In some embodiments, lines 614a and 614b may be closer toward the center of display 602 or away from the center of display 602 to cover a predetermined center portion of field of view representation 612. For example, in some embodiments, center portion 614 includes 30%, 40%, 50%, 60%, and/or 70% of field of view representation 612 based on a position of lines 614a and 614b with respect to the center of display 602.

When electronic device 600 operates the distancing feature in the first mode, an entity that is outside of center portion 614 is optionally not detected by electronic device 600 and an indication of distance to an entity that is outside of center portion 614 is not displayed on distancing user interface 610. At FIG. 6C, first person 612a is within center portion 614 of field of view representation 612, but second person 612b is outside of center portion 614 of field of view representation 612. Accordingly, electronic device 600 does not cause display of an indication of distance to second person 612b because second person 612b is not positioned within center portion 614 of field of view representation 612. At FIG. 6C, second person 612b is positioned closer to electronic device 600 (and the user of electronic device 600) than first person 612a. However, because second person 612b is not within center portion 614 of field of view representation 612, electronic device 600 does not display an indication of distance between electronic device 600 and second person 612b.

At FIG. 6C, electronic device 600 detects first person 612a because first person is the closest entity (e.g., object and/or person) to electronic device 600 that is positioned within center portion 614 of field of view representation 612. In response to detecting first person 612*a* within center portion 614 of field of view representation 612, electronic device 600 displays first distance indicator 616 and second distance indicator 618. First distance indicator 616 and second distance indicator 618 may provide visual confirmation to the user of electronic device 600 that the distancing feature is activated on electronic device 600. Additionally, electronic device 600 displays distancing feature indicator 610*b* on distancing user interface 610 to indicate that the distancing feature is activated. First distance indicator 616 is a visual representation of a distance between electronic device 600 and first person 612*a*. At FIG. 6C, first distance indicator 616 is a dashed or dotted line having a start point 616*a* and an end point 616*b*. Start point 616*a* represents a position of electronic device 600 (and/or the user of electronic device 600) within field of view representation 612. At FIG. 6C, start point 616*a* is positioned above and adjacent to second distance indicator 618 on display 602 as a reference point to indicate the position of electronic device 600 on field of view representation 612. Displaying start point 616*a* of first distance indicator 616 above and adjacent to second distance indicator 628 facilitates a user's understanding that first distance indicator 616 and second distance indicator 618 are related (e.g., second distance indicator 618 provides further, textual context for the visual representation of distance provided by first distance indicator 616). In some embodiments, start point 616*a* is positioned at the bottom of display 602 and below second distance indicator 618.

End point 616*b* of first distance indicator 616 is displayed as being positioned proximate to (or adjacent to) first person 612*a* within field of view representation 612. In some embodiments, end point 616*b* is displayed on field of view representation 612 proximate to a portion of first person 612*a* that is detected by electronic device 600 as being closest to electronic device 600. For example, when first person 612*a* is facing the user of electronic device 600 and sitting down, end point 616*b* can be positioned on field of view representation 612 proximate to a foot of first person 612*a* (e.g., the foot of first person 612*a* is closer to electronic device 600 than other portions of the body of first person 612*a* when first person 612*a* is sitting down and facing the user of electronic device 600). In some embodiments, end point 616*b* is positioned within field of view representation 612 at (or near) a mid-point of a body of first person 612*a* and/or another entity that is determined to be the closest distance to electronic device 600 and is within field of view representation 612.

As set forth above, at FIG. 6C, first distance indicator 616 includes a dashed and/or dotted line between a detected entity within center portion 614 and electronic device 600. The dashed and/or dotted line of first distance indicator 616 continuously increases from start point 616*a* to end point 616*b*. For example, dots of first distance indicator 616 steadily increase in diameter from start point 616*a* to end point 616*b* (e.g., sequentially). In some embodiments, dashes of first distance indicator 616 steadily increase in thickness and/or length from start point 616*a* to end point 616*b* (e.g., sequentially). In some embodiments, first distance indicator 616 does not increase from start point 616*a* to end point 616*b*, but instead maintains a diameter of dots and/or a thickness/length of dashes from start point 616*a* to end point 616*b*.

At FIG. 6C, second distance indicator 618 is a textual representation (e.g., numeric representation) of the distance between first person 612*a* and electronic device 600. In other words, second distance indicator 618 provides a numeric value of an estimate of distance between first person 612*a* and electronic device 600. In some embodiments, electronic device 600 estimates the distance between first person 612*a* and electronic device 600 using the camera of electronic device 600. In some embodiments, electronic device 600 includes multiple cameras and estimates the distance between first person 612*a* and electronic device 600 via parallax analysis with information (e.g., displacement, position, and/or angle information of a detected entity from a line of sight) received from two or more cameras of electronic device 600 to. In some embodiments, electronic device 600 generates a depth map using information (e.g., displacement, position, and/or angle information of a detected entity from a line of sight) received from the two or more cameras of electronic device 600 to estimate the distance between first person 612*a* and electronic device 600.

In some embodiments, electronic device 600 displays second distance indicator 618 with a rounded numerical value of distance (e.g., estimated distance) between first person 612*a* and electronic device 600. For example, electronic device 600 rounds an estimated distance determined from information received from one or more cameras of electronic device 600 to one or two significant figures. In some embodiments, electronic device 600 rounds the estimated distance to one significant figure when second distance indicator 618 represents a first metric (e.g., feet). In some embodiments, electronic device rounds the estimated distance to two significant figures when second distance indicator 618 represents a second metric (e.g., meters). As set forth below with reference to FIG. 6M, electronic device 600 displays second distance indicator 618 with a particular metric (e.g., feet or meters) based on a metric setting selected by user of electronic device 600.

As set forth above, when operating in the first mode of the distancing feature, electronic device 600 detects the closest entity to electronic device 600 within center portion 614 of field of view representation 612. As such, electronic device 600 forgoes display of first distance indicator 616 and second distance indicator 618 for entities that are detected within center portion 614, but are determined to be a farther distance from electronic device 600 than a closest entity within center portion 614.

Figure 6E:
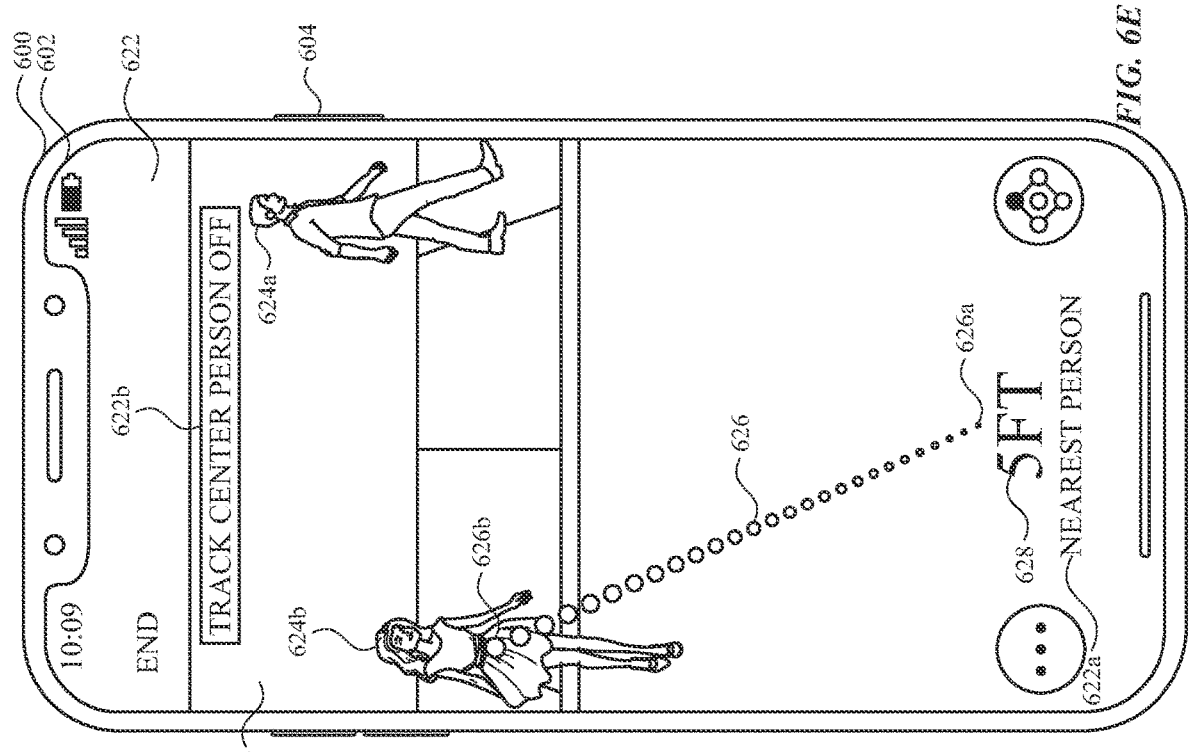
Figure 6D:
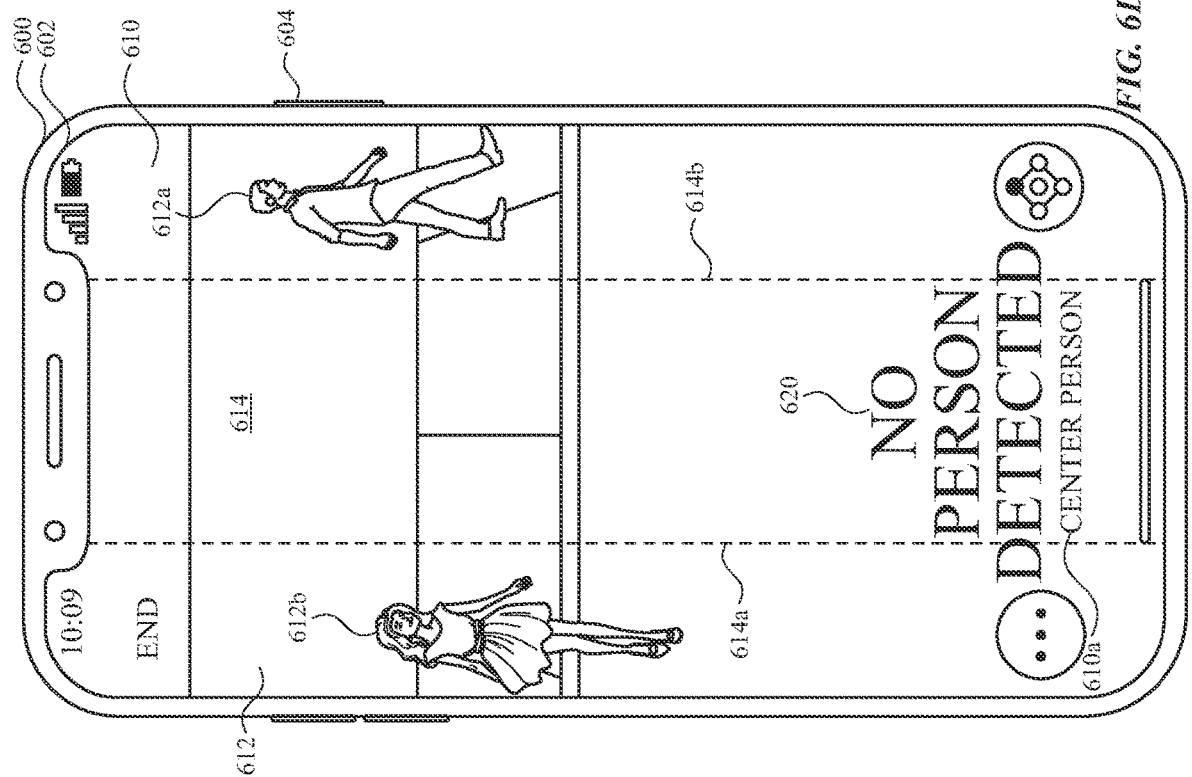

At FIG. 6D, first person 612*a* is positioned (e.g., moved) outside of center portion 614 of field of view representation 612 and second person 612*b* remains positioned outside of center portion 614. Accordingly, electronic device forgoes display of first distance indicator 616 and second distance indicator 618 because no entity is detected within center portion 614 of field of view representation 612 (e.g., between lines 614*a* and 614*b*, which are not displayed on distancing user interface 610). At FIG. 6D, electronic device 600 displays indicator 620 (e.g., "No Person Detected") indicating that no entity is positioned and/or detected within center portion 614 of field of view representation 612. In some embodiments, electronic device 600 forgoes display of first distance indicator 616 and second distance indicator 618 and displays indicator 620 when an entity is detected and positioned within center portion 614, but electronic device 600 determines that the distance between the detected entity and electronic device 600 is beyond a threshold distance (e.g., 10 feet, 15 feet, and/or 20 feet).

As set forth above, electronic device 600 can operate using two different modes of the distancing feature. In some embodiments, electronic device 600 switches from the first mode of the distancing feature to the second mode of the distancing feature via user input on mode indicator 610*a* displayed in distancing user interface 610. In some embodiments, electronic device 600 switches from the first mode of the distancing feature to the second mode of the distancing feature via user input on distancing settings user interface 656, shown at FIG. 6M. In some embodiments, electronic device 600 switches from the first mode of the distancing feature to the second mode of the distancing feature in response to a custom (e.g., user-specified) user input, such as a long press gesture on display 602 when distancing user interface 610 is displayed and/or a single or multi-tap (or multi-press) gesture on side button 604 when distancing user interface 610 is displayed.

In response to detecting the user input that causes electronic device 600 to switch from the first mode of the distancing feature to the second mode of the distancing feature, electronic device 600 displays distancing user interface 622, as shown at FIG. 6E. At FIG. 6E, the second mode of the distancing feature is activated by electronic device 600 and the first mode of the distancing feature is deactivated by electronic device 600. Distancing user interface 622 includes indicator 622*b* indicating that the first mode has been deactivated (e.g., "Track Center Person Off"). When operating in the second mode of the distancing feature, electronic device 600 detects a closest entity within any portion of field of view representation 624 of distancing user interface 622 (as opposed to only detecting entities that are positioned within center portion 614 of field of view representation 612, as described above with reference to FIGS. 6C and 6D). Accordingly, the second mode of the distancing feature enables a user of electronic device 600 to determine a closest entity to electronic device 600 (and to the user holding electronic device 600) within field of view representation 624, whereas the first mode of the distancing feature enables a user of electronic device 600 to determine a closest entity that is in front of (e.g., positioned in center portion 614 of field of view representation 612) electronic device 600 (and in front of the user holding electronic device 600). Thus, a user of electronic device 600 may activate the first mode of the distancing feature when walking and/or moving to determine an entity that is closest to the user and in front of the user when walking and/or moving. Alternatively, the user of electronic device 600 may activate the second mode of the distancing feature when stationary (e.g., standing, sitting, and/or laying down) to determine an entity that is closest to the user and within the field of view of a camera of electronic device 600.

At FIG. 6E, distancing user interface 622 includes field of view representation 624 that includes first person 624*a* (e.g., first person 612*a*) and second person 624*b* (e.g., second person 612*b*). First person 624*a* and second person 624*b* are both within field of view representation 624, and because the second mode of the distancing feature is activated, electronic device 600 detects second person 624*b* because second person 624*b* is determined to be closer to electronic device 600 than first person 624*a*. When operating in the second mode of the distancing feature, electronic device 600 can detect multiple entities within field of view representation 624, but optionally displays indicators of distance to the closest detected entity within field of view representation 624 (e.g., without displaying indicators to other entities). The user of electronic device 600 may have the need to determine how far away the user is positioned to the closest entity without needing to determine the distance to entities that are farther away than the closest entity within field of view representation 624.

At FIG. 6E, distancing user interface 622 includes first distance indicator 626 and second distance indicator 628, which both indicate a distance between electronic device 600 and second person 624*b*. However, electronic device 600 forgoes display of a distance indicator (e.g., first distance indicator 626 and second distance indicator 628) for first person 624*a* because first person 624*a* is determined to be positioned a greater distance away from electronic device 600 than second person 624*b*. As set forth above, first distance indicator 626 and second distance indicator 628 provide visual confirmation to the user of electronic device 600 that the distancing feature is activated on electronic device 600. First distance indicator 626 is a visual representation of a distance between electronic device 600 and first person 624*a*. At FIG. 6E, first distance indicator 626 is a dashed or dotted line having a start point 626*a* and an end point 626*b*. Start point 626*a* represents a position of electronic device 600 (and/or the user of electronic device 600) within field of view representation 624. At FIG. 6E, start point 626*a* is positioned above and adjacent to second distance indicator 628 on display 602 as a reference point to indicate the position of electronic device 600 on field of view representation 624. In some embodiments, start point 626*a* is positioned at the bottom of display 602 and below second distance indicator 628.

End point 626*b* is displayed as being positioned proximate to second person 624*b* within field of view representation 624. In some embodiments, end point 626*b* is displayed on field of view representation 624 proximate to a portion of second person 624*b* that is detected by electronic device 600 as being closest to electronic device 600. For example, when second person 624*b* is facing the user of electronic device 600 and sitting down, end point 626*b* can be positioned on field of view representation 624 proximate to a foot of second person 624*b* (e.g., the foot of second person 624*b* is closer to electronic device 600 than other portions of the body of second person 624*b* when second person 624*b* is sitting down and facing the user of electronic device 600). In some embodiments, end point 626*b* is displayed at (or near) a midpoint of a body of second person 624*b*, as shown at FIG. 6E.

As set forth above, at FIG. 6E, first distance indicator 626 includes a dashed and/or dotted line between a closest detected entity within field of view representation 624 and electronic device 600. The dashed and/or dotted line of first distance indicator 626 continuously increases from start point 626*a* to end point 626*b*. For example, dots of first distance indicator 626 steadily increase in diameter from start point 626*a* to end point 626*b*. In some embodiments, dashes of first distance indicator 626 steadily increase in thickness and/or length from start point 626*a* to end point 626*b*. In some embodiments, first distance indicator 626 does not continuously increase in diameter and/or thickness/length from start point 626*a* to end point 626*b*.

At FIG. 6E, second distance indicator 628 is a textual representation (e.g., numeric representation) of the distance between second person 624*b* and electronic device 600. In other words, second distance indicator 628 provides a numeric value of an estimate of distance between second person 624*b* and electronic device 600. In some embodiments, electronic device 600 estimates the distance between second person 624*b* and electronic device 600 using the camera of electronic device 600. In some embodiments, electronic device 600 includes multiple cameras and estimates the distance between second person 624*b* and electronic device 600 via parallax analysis with information (e.g., displacement, position, and/or angle information of a detected entity from a line of sight) received from two or more cameras of electronic device 600. In some embodiments, electronic device 600 generates a depth map using information (e.g., displacement, position, and/or angle information of a detected entity from a line of sight) received from the two or more cameras of electronic device 600 to estimate the distance between second person 624b and electronic device 600.

In some embodiments, electronic device 600 displays second distance indicator 628 with a rounded numerical value of distance between second person 624b and electronic device 600. For example, electronic device 600 rounds an estimated distance determined from information received from one or more cameras of electronic device 600 to one or two significant figures. In some embodiments, electronic device 600 rounds the estimated distance to one significant figure when second distance indicator 628 represents a first metric (e.g., feet). In some embodiments, electronic device 600 rounds the estimated distance to two significant figures when second distance indicator 628 represents a second metric (e.g., meters). As set forth below with reference to FIG. 6M, electronic device 600 displays second distance indicator 628 (and second distance indicator 618) with a particular metric (e.g., feet or meters) based on a metric setting selected by the user of electronic device 600.

At FIG. 6E, electronic device 600 displays first distance indicator 626 and second distance indicator 628 to provide an indication of distance between electronic device 600 and second person 624b because second person 624b is determined to be closest to electronic device 600 (e.g., based on data and/or information received from one or more cameras of electronic device 600). At FIG. 6F, field of view representation 624 includes first person 624a, second person 624b, and third person 624c (e.g., third person 624c has moved into the field of view of one or more cameras of electronic device). Second person 624b is positioned closer to electronic device 600 as compared to the position of second person 624b shown in FIG. 6E (e.g., second person 624b is positioned 4 feet from electronic device 600 instead of 5 feet from electronic device 600). At FIG. 6F, second person 624b is still the closest entity (e.g., person and/or object) detected within field of view representation 624 to electronic device 600. Accordingly, distancing user interface 622 includes first distance indicator 626 and second distance indicator 628 that provide an indication of distance between second person 624b and electronic device 600. In addition, electronic device 600 does not display (e.g., forgoes display of) distance indicators that provide an indication of distance between first person 624a and/or third person 624a because second person 624b is determined to be closest to electronic device 600.

At FIG. 6F, electronic device 600 causes audio output as shown by audio indicator 630 and haptic output as shown by haptic indicators 632. In some embodiments, electronic device 600 causes audio output and/or haptic output when an entity within the field of view representation 624 is determined to be positioned within a threshold distance range from electronic device 600 (e.g., positioned at or less than 6 feet from electronic device 600). As such, electronic device 600 outputs audio and/or haptics to alert the user of electronic device 600 that an entity is detected as being within the threshold distance range from electronic device 600. In some embodiments, the audio output shown by audio indicator 630 is an alert that does not include speech (e.g., an alarm sound and/or an audio tone). In some embodiments, the audio output shown by audio indicator 630 includes audio having speech that provides additional information to the user, such as information related to a distance between electronic device 600 and the closest detected entity within field of view representation 624 (e.g., second person 624b). As described below with reference to FIG. 6M, electronic device 600 adjusts audio output and haptic output based on user inputs detected by electronic device 600 when distancing settings user interface 656 is displayed.

At FIG. 6G, first person 624a and second person 624b maintain their respective positions within field of view representation 624 and third person 624c is positioned closest to electronic device 600 within field of view representation 624 (e.g., third person 624c has moved and/or walked closer to the user holding electronic device 600 or vice versa). At FIG. 6G, electronic device 600 adjusts first distance indicator 626 to provide a visual indication of distance between third person 624c and electronic device 600 instead of a visual indication of distance between second person 624b and electronic device 600 (e.g., because third person 624c is detected to be closer to electronic device 600 than second person 624b). As such, end point 626b of first distance indicator 626 is displayed at a position on field of view representation 624 that is proximate to third person 624c instead of second person 624b. As shown at FIG. 6G, electronic device 600 maintains the position of start point 626a of first distance indicator 626 at a position above second distance indicator 628. Accordingly, electronic device 600 moves and/or adjusts first distance indicator 626 to provide the visual indication of distance between the closest entity within field of view representation 624 and electronic device 600.

Also, electronic device 600 updates second distance indicator 628 to provide a textual (e.g., numeric) representation of distance between third person 624c and electronic device 600. As such, second distance indicator 628 provides the textual representation of distance between the closest entity detected within field of view representation 624 and electronic device 600. Positioning start point 626a of first distance indicator 626 directly above second distance indicator 628 facilitates a user's understanding that second distance indicator 628 is associated with first distance indicator 626 and provides the textual representation of distance between the closest entity detected within field of view representation 624 (e.g., third person 624c) and electronic device 600.

At FIG. 6G, second distance indicator 628 indicates that third person 624c is positioned at a distance closer to electronic device 600 when compared to the distance between second person 624b and electronic device 600 in FIG. 6F (e.g., 2 feet instead of 4 feet). At FIG. 6G, electronic device 600 outputs audio, as indicated by audio indicator 634, and outputs haptic feedback, as indicated by haptic indicator 636. In some embodiments, electronic device 600 maintains audio output and haptic feedback output while displaying distancing user interface 622 (and/or distancing user interface 610) and when electronic device 600 determines that an entity in field of view representation 624 is within the threshold distance range (e.g., a distance at or within 6 feet between electronic device 600 and the closest entity within field of view representation 624).

At FIG. 6G, audio indicator 634 indicates that electronic device 600 outputs audio differently when compared to audio indicator 630 of FIG. 6F (e.g., as indicated by two musical notes instead of one musical note) because third person 624c is determined to be closer to electronic device 600 in FIG. 6G than second person 624b in FIG. 6F. In some embodiments, electronic device 600 adjusts audio output based on the determined distance between electronic device 600 and the closest entity within field of view representation 624. For example, electronic device 600 may increase a volume level of the audio output, increase a frequency of the audio output, and/or increase a pitch of the audio output as the distance between the closest entity within field of view representation 624 and electronic device 600 decreases. Similarly, electronic device 600 may reduce a volume level of the audio output, decrease a frequency of the audio output, and/or decrease a pitch of the audio output as the distance between the closest entity within field of view representation 624 and electronic device 600 increases. As such, users that are vision impaired may listen to the audio output instead of viewing distancing user interface 622 to determine an estimate of a distance between the user and the closest entity within field of view representation 624.

As set forth above, in some embodiments, electronic device 600 causes audio output that includes speech. Electronic device 600 can also adjust the volume level, frequency, and/or pitch of audio output that includes speech based on the determined distance between electronic device 600 and the closest entity within field of view representation 624. In some embodiments, the audio output that includes speech includes information related to the distance between electronic device 600 and the closest entity detected within field of view representation 624. For instance, the audio output that includes speech can include voice audio that outputs speech indicating (speaking) the distance between electronic device 600 and the closest entity detected within field of view representation 624.

At FIG. 6G, haptics indicator 636 indicates that electronic device 600 outputs haptic feedback differently when compared to haptics indicator 632 of FIG. 6F (e.g., as indicated by an additional mark representing haptic feedback) because third person 624c is determined to be closer to electronic device 600 in FIG. 6G than second person 624b in FIG. 6F. In some embodiments, electronic device 600 adjusts haptic output based on the determined distance between electronic device 600 and the closest entity within field of view representation 624. For example, electronic device 600 may increase an intensity level of the haptic output, increase a frequency of the haptic output, and/or increase a pitch of the haptic output as the distance between the closest entity within field of view representation 624 and electronic device 600 decreases. Similarly, electronic device 600 may reduce an intensity level of the haptic output, decrease a frequency of the haptic output, and/or decrease a pitch of the haptic output as the distance between the closest entity within field of view representation 624 and electronic device 600 increases. As such, users that are vision impaired may sense (e.g., feel) the haptic output instead of viewing distancing user interface 622 to determine an estimate of a distance between the user and the closest entity within field of view representation 624.

Accordingly, in addition to electronic device 600 displaying first distance indicator 626 and second distance indicator 628, electronic device 600 is also configured to output audio and/or haptic feedback to provide an indication of distance between electronic device 600 and the closest entity within field of view representation 624. Thus, users that are vision impaired can sense (e.g., hear and/or feel) the audio and/or haptic feedback to determine an estimated distance between the user and the closest entity within field of view representation 624.

Figure 6I:
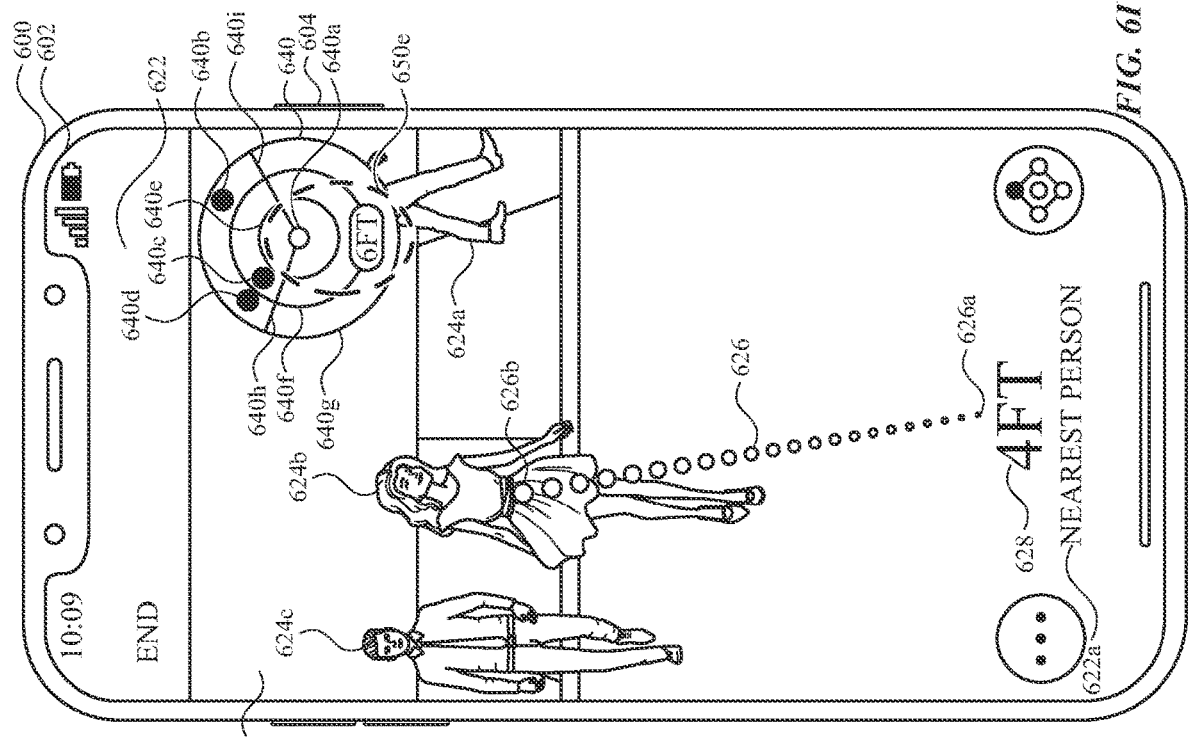
Figure 6H:
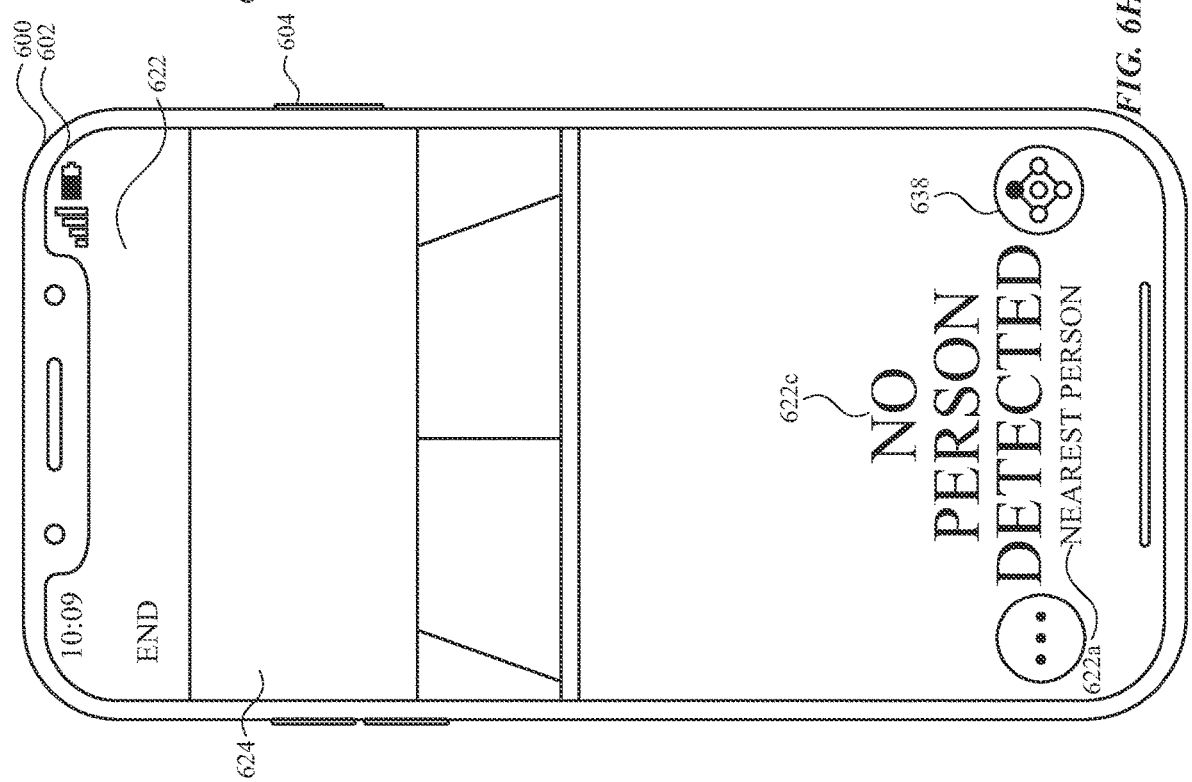

At FIG. 6H, field of view representation 624 no longer includes first person 624a, second person 624b, and third person 624c. As such, electronic device 600 does not detect any entity within field of view representation 624. At FIG. 6H, electronic device 600 displays distancing user interface 622 with indicator 622c indicating that an entity is not detected within field of view representation 624 (e.g., "No Person Detected"). In some embodiments, electronic device 600 replaces display of second distance indicator 628 with indicator 622c and ceases to display first distance indicator 626. Further, electronic device 600 can cease audio output and haptic output to further indicate to the user of electronic device 600 that an entity is not within field of view representation 624.

As set forth above, in some embodiments, electronic device 600 displays indicator 622c on distancing user interface 622 when an entity is within field of view representation 624, but the entity is determined to be positioned at a distance beyond a threshold distance range (e.g., 10 feet, 15 feet, 20 feet) from electronic device 600. For instance, even though an entity is displayed and/or detected within field of view representation 624, electronic device 600 displays indicator 622c in response to a determination that the entity is positioned a distance beyond the threshold distance range from electronic device 600.

Turning back to FIG. 6F, electronic device 600 detects user input 650d on mapping toggle user interface object 638 of distancing user interface 622. In response to detecting user input 650d, electronic device 600 displays distancing user interface 622 including mapping user interface object 640, as shown at FIG. 6I. In some embodiments, electronic device 600 does not display mapping user interface object 638 on distancing user interface 622 (and/or distancing user interface 610). In some embodiments, electronic device displays distancing user interface object 608g instead of mapping user interface object 638, such that distancing user interface object 608g acts as a toggle to activate and deactivate the distancing feature on electronic device 600.

At FIG. 6I, field of view representation 624 includes first person 624a, second person 624b, and third person 624c. As set forth above with reference to FIG. 6F, electronic device 600 determines that second person 624b is the closest entity to electronic device 600 within field of view representation 624. Thus, distancing user interface 622 includes first distance indicator 626 and second distance indicator 628, which provide an indication of the distance between second person 624b and electronic device 600. In addition, distancing user interface 622 includes mapping user interface object 640 that provides an indication of distance between electronic device 600 and entities within and/or outside of field of view representation 624. At FIG. 6I, mapping user interface object 640 includes first indicator 640a corresponding to a position of electronic device 600 (and thus the user holding electronic device 600), second indicator 640b corresponding to a position of first person 624a with respect to the position of electronic device 600, third indicator 640c corresponding to a position of second person 624b with respect to the position of electronic device 600, and fourth indicator 640d corresponding to a position of third person 624c with respect to the position of electronic device 600.

Further, mapping user interface object 640 includes first distance ring 640e corresponding to a first predetermined distance (e.g., 3 feet) from electronic device 600, second distance ring 640f corresponding to a second predetermined distance (e.g., 6 feet), greater than the first predetermined distance, from electronic device 600, and third distance ring 640g corresponding to a third predetermined distance (e.g., 9 feet), greater than the first and second predetermined distances, from electronic device 600. First distance ring 640e, second distance ring 640f, and third distance ring 640g enable a user of electronic device 600 to easily understand a proximity of all detected entities to the user based on the positions of indicators 640*a*-640*d* within first distance ring 640*e*, second distance ring 640*f*, and third distance ring 640*g*.

Further still, mapping user interface object 640 includes first field of view indicator 640*h* and second field of view indicator 640*i*, which represent a position of field of view indicator 624 on mapping user interface object 640. Mapping user interface object 640 represents an area surrounding electronic device 600 (and user holding electronic device 600) that extends beyond field of view indicator 624. In some embodiments, mapping user interface object 640 represents an area corresponding to 360 degrees about the position of electronic device 600 (e.g., the position represented by first indicator 640*a*). As such, first field of view indicator 640*h* and second field of view indicator 640*i* enable a user to determine where entities have been detected within field of view representation 624 as well as outside of field of view representation 624.

In some embodiments, mapping user interface object 640 tracks movement of entities detected within field of view representation 624 in real time while field of view representation 624 is displayed 624, but does not update movement of entities detected outside of field of view representation 624 (e.g., movement of a person that is no longer within field of view representation 624). In some embodiments, mapping user interface object 640 tracks movement of entities detected within field of view representation 624 at a predetermined time interval (e.g., every half second, every second, and/or every ten seconds) while field of view representation 624 is displayed 624, but does not update movement of entities detected outside of field of view representation 624 (e.g., movement of a person that is no longer within field of view representation 624).

At FIG. 6I, electronic device 600 detects user input 650*e* (e.g., a tap gesture) on mapping user interface object 640. In response to detecting user input 650*e* on mapping user interface object 640, electronic device 600 displays enlarged mapping user interface object 642, as shown at FIG. 6J. At FIG. 6J, enlarged mapping user interface object 642 overlaps and/or at least partially covers field of view representation 624. Also at FIG. 6J, enlarged mapping user interface object 642 includes substantially the same components as mapping user interface object 640 (e.g., components 640*a*-640*i*). Accordingly, a user who is vision impaired may view and comprehend distances between of detected entities, both within the currently displayed field of view representation 624 and outside of the currently displayed field of view representation 624, and electronic device 600. At FIG. 6J, electronic device 600 detects user input 650*f* (e.g., a tap gesture) on end user interface object 644 of distancing user interface 622. In response to detecting user input 650*f* on end user interface object 644, electronic device 600 deactivates the distancing feature, and displays user interface 608, as shown at FIG. 6B.

As set forth above, at FIG. 6B, electronic device 600 can detect user input 650*c* on settings user interface object 608*h*. In response to detecting user input 650*c* on settings user interface object 608*h*, electronic device 600 displays settings menu 608*j*, as shown at FIG. 6K.

At FIG. 6K, settings menu 608*j* includes general settings user interface object 646, distancing user interface object 648, and magnifier user interface object 652. Electronic device 600 displays distancing user interface 610 and/or distancing user interface 622 in response to detecting user input on distancing user interface object 648. Additionally, electronic device 600 displays user interface 608 in response to detecting user input on magnifier user interface object 652. As such, electronic device 600 is configured to activate and deactivate the distancing feature in response to user input on distancing user interface object 648 and magnifier user interface object 652, respectively. At FIG. 6K, electronic device 600 detects user input 650*g* (e.g., a tap gesture) on general settings user interface object 646. In response to detecting user input 650*g* on general settings user interface object 646, electronic device 600 displays general settings user interface 654, as shown at FIG. 6L.

At FIG. 6L, general settings user interface 654 includes first settings area 654*a*, second settings area 654*b*, filter settings user interface object 656*c*, and distancing settings user interface object 656*d*. In some embodiments, first settings area 654*a* and second settings area 654*b* correspond to user interface objects that electronic device 600 is configured to display on user interface 608. As such, electronic device 600 can display and/or cease to display user interface objects on user interface 608 in response to detecting user input in first settings area 654*a* and/or second settings area 654*b*. At FIG. 6L, electronic device 600 detects user input 650*h* (e.g., a tap gesture) on distancing settings user interface object 656*d*. In response to detecting user input 650*h*, electronic device 600 displays distancing settings user interface 656, as shown at FIG. 6M.

At FIG. 6M, distancing settings user interface 656 includes metric settings area 658, mode settings area 660, and feedback settings area 662. Metric settings area 658 includes first metric user interface object 658*a* (e.g., "Meters") and second metric user interface object 658*b* (e.g., "Feet"). At FIG. 6M, distancing settings user interface 656 includes indicator 658*c* indicating that the second metric corresponding to second metric user interface object 658*b* is currently selected and/or activated. As set forth above, electronic device 600 can adjust a metric that is indicated by second distance indicator 618 and second distance indicator 628 in response to detecting user input on first metric user interface object 658*a* and/or second metric user interface object 658*b*. Further, electronic device 600 may round a numerical value indicated by second distance indicator 618 and second distance indicator 628 differently based on whether user input is detected on first metric user interface object 658*a* or second metric user interface object 658*b*. For example, electronic device 600 can display second distance indicator 618 and second distance indicator 628 with a numeric value indicating an estimated distance rounded to two significant figures in response to detecting user input on first metric user interface object 658*a*. Electronic device 600 can display second distance indicator 618 and second distance indicator 628 with a numeric value indicating an estimated distance rounded to one significant figure in response to detecting user input on second metric user interface object 658*b*. In some embodiments, electronic device 600 may display second distance indicator 618 and second distance indicator 628 with a numeric value indicating an estimated distance rounded to the same significant figure regardless of whether first metric user interface object 658*a* or second metric user interface object 658*b* is selected.

Mode settings area 660 includes first mode user interface object 660*a* corresponding to the first mode of the distancing feature of electronic device 600 and second mode user interface object 660*b* corresponding to the second mode of the distancing feature of electronic device 600. At FIG. 6M, distancing settings user interface 656 includes indicator 660*c* indicating that the first mode of the distancing feature associated with first mode user interface object 660*a* is selected and/or activated. As set forth above, the first mode of the distancing feature of electronic device 600 detects an entity that is closest to electronic device 600 within center portion 614 of field of view representation 612. The second mode of the distancing feature of electronic device 600 detects an entity that is closest to electronic device 600 that is positioned at any location within field of view representation 624. Accordingly, electronic device 600 displays distancing user interface 610 when first mode user interface object 660*a* is selected and/or activated and displays distancing user interface object 622 when second mode user interface object 660*b* is selected and/or activated.

Feedback settings area 662 includes sounds user interface object 662*a* (e.g., a first toggle) corresponding to activating or deactivating first audio output that does not include speech by electronic device 600 when the distancing feature is activated. Feedback settings area 662 also includes speech user interface object 662*b* (e.g., a second toggle) corresponding to activating or deactivating second audio output that does include speech by electronic device 600 when the distancing feature is activated. Further, feedback settings area 662 includes haptics user interface object 662*c* (e.g., a third toggle) corresponding to activating or deactivating haptic feedback by electronic device 600 when the distancing feature is activated. As set forth above, in some embodiments, electronic device 600 outputs first audio output, second audio output, and/or haptics feedback when an entity detected by electronic device (e.g., within center portion 614 of field of view representation 612 and/or within field of view representation 624) is determined to be within a distance threshold range (e.g., 6 feet) from electronic device 600. Further, as set forth above, electronic device 600 is configured to adjust output of the first audio output, the second audio output, and/or haptics feedback based on the determined distance between the detected entity and electronic device 600.

FIG. 7 is a flow diagram illustrating a method for providing an indication of distance to an entity using computer system in accordance with some embodiments. Method 700 is performed at a computer system (e.g., 100, 300, 500, 600) (e.g., a smart device, such as a smartphone or a smartwatch; and/or a mobile device) that is in communication with one or more cameras (e.g., one or more cameras (e.g., dual cameras, triple cameras, quad cameras, etc.) on the same or different sides of the computer system (e.g., front cameras, back cameras)) and a display generation component (e.g., a display, and/or a touch screen). Some operations in method 700 are, optionally, combined, the orders of some operations are, optionally, changed, and some operations are, optionally, omitted.

The computer system (e.g., 600) displays (702), via the display generation component, a visual representation (e.g., 612, 624) of a field of view of (e.g., a first camera of) the one or more cameras (e.g., a viewfinder, a live viewfinder, and/or a visual representation of a portion of an area and/or scene surrounding the computer system that is currently within a field of view of the one or more cameras).

In some embodiments, the computer system detects (e.g., via the one or more cameras, via a depth of field camera/sensor) an entity (e.g., a person and/or an object (e.g., a non-person)) within the field of view of the one or more cameras.

In some embodiments, the computer system determines (e.g., in response to detecting the entity in the field of view; and/or subsequent to detecting the entity in the field of view) a distance (e.g., from the computer system) to the entity. In some embodiments, the distance is determined via parallax between two (or more) cameras of the one or more cameras and/or via a depth map generated via one or two (or more) cameras of the one or more cameras.

In accordance with (704) a determination that an entity (e.g., 612*a*, 612*b*, 612*c*) meets a set of detection criteria, the set of detection criteria including a first criterion that is met when the entity is detected within the field of view of the one or more cameras, the computer system (e.g., 600) provides (706), concurrently with the visual representation (e.g., 612, 624) of the field of view that includes the entity (e.g., concurrently with the detected entity in the visual representation of the field of view of the one or more cameras; and/or overlaid on the visual representation of the field of view), one or more indicators of distance between the computer system and the entity, wherein providing the one or more indicators of distance includes: displaying, via the display generation component, a visual distance indicator (e.g., 616, 618, 626, 628) (e.g., a line (e.g., a dashed line or solid line) that includes a length indicative of the distance, and/or a numeric value indicative of the distance) that indicates the distance between the computer system and the entity; and In some embodiments, the visual distance indicator includes a numeric value that corresponds to the distance between the detected entity and the computer system, such as a numeric value that is rounded to within one or two significant figures. In some embodiments, the computer system detects a plurality of entities concurrently within the field of view of the one or more cameras and displays the visual distance indicator for only the closest detected entity of the plurality of detected entities.

In accordance with (708) a failure to determine that an entity meets the set of detection criteria (e.g., a determination that no entity is detected that meets the set of detection criteria), the computer system (e.g., 600) forgoes providing (710) the one or more indicators of a distance between the computer system and the entity.

In some embodiments, the one or more indicators of distance varies over time as (e.g., in conjunction with) the distance between the computer system and the entity varies over time.

Providing indicators (including a visual indicator) of distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, providing (706) the one or more indicators of the distance includes: providing (e.g., outputting via an audio output at a speaker of the computer system and/or transmitting to wireless headphones in communication with the computer system for audio output) an audio distance indicator output (e.g., 630, 634) that changes based on the distance between the computer system and the entity.

Providing indicators (including an audio indicator) of distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the audio changes over time as the distance between the computer system and the entity changes, the audio being based on the current distance. In some embodiments, the audio is continuous. In some embodiments, the audio is recurring.

In some embodiments, a pitch of the audio distance indicator output (e.g., 630, 634) becomes higher as the distance between the computer system and the entity decreases, a frequency (e.g., rate of beeps/sound and/or how often a repeating sound is produced) of the audio distance indicator output (e.g., 630, 634) becomes higher as the distance between the computer system and the entity decreases, or (optionally, and) a volume (e.g., loudness) of the audio distance indicator output (e.g., 630, 634) increases as the distance between the computer system and the entity decreases.

In some embodiments, a pitch of the audio distance indicator output becomes higher as the distance between the computer system and the entity decreases.

Providing indicators (including an audio indicator) of change in distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the pitch of the audio distance indicator output changes based on the distance between the computer system and the entity. In some embodiments, the pitch becomes lower as the distance between the computer system and the entity increases. In some embodiments, the pitch remains constant as the distance between the computer system and the entity remains constant.

In some embodiments, a frequency (e.g., rate of beeps/sound and/or how often a repeating sound is produced) of the audio distance indicator output becomes higher as the distance between the computer system and the entity decreases.

Providing indicators (including an audio indicator) of change in distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the frequency of the audio distance indicator output changes based on the distance between the computer system and the entity. In some embodiments, the frequency becomes lower as the distance between the computer system and the entity increases. In some embodiments, the frequency remains constant as the distance between the computer system and the entity remains constant.

In some embodiments, a volume (e.g., loudness) of the audio distance indicator output increases as the distance between the computer system and the entity decreases.

Providing indicators (including an audio indicator) of change in distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the volume of the audio distance indicator output changes based on the distance between the computer system and the entity. In some embodiments, the volume reduces as the distance between the computer system and the entity increases. In some embodiments, the volume remains constant as the distance between the computer system and the entity remains constant.

In some embodiments, the audio distance indicator output (e.g., 630, 634) includes stereo components, the stereo components including a first audio channel with a first characteristic (e.g., a first volume, a first pitch, a first spatial filter applied) and a second audio channel with a second characteristic (e.g., a second volume, a second pitch, a second spatial filter applied) that is different from the first characteristic, the first characteristic and the second characteristic based on the distance between the computer system and the entity.

Providing indicators, such as stereo or spatial audio indicators, of distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the first audio channel (e.g., left channel) is different from the second audio channel (e.g., right audio channel). In some embodiments, the first audio channel and the second audio channel are produced based on a direction and/or location of the entity with respect to the computer system or the user. In some embodiments, the stereo components are generated such that a user of the computer system perceives audio of the audio distance indicator output as originating from a direction that corresponds to a direction of the entity with respect to the computer system or the user.

In some embodiments, the stereo component includes spatial audio. Spatial audio includes audio characteristics of sound have been modified (e.g., by applying filters) such that a user (e.g., listener) perceives the sound as being emitted from a particular location in space (e.g., three-dimensional (3D) space). Such techniques can be achieved using speakers, such as headphones, earbuds, or loudspeakers. In some examples, such as when the user is using headphones, a binaural simulation is used to recreate binaural cues that give the user the illusion that sound is coming from a particular location in space. For example, the user perceives the source of the sound as coming from the left of the user. For another example, the user perceives the source of the sound as coming from a particular direction and/or distance relative to the user. For another example, the user perceives the source of the sound as passing by from left to right in front of the user. This effect can be enhanced by using head tracking to adjust the binaural filters to create the illusion that the location of the source of the sound stays static in space with respect to the user and/or tracks the location of the entity in space with respect to the user, even when the user's head moves or rotates. In some examples, such as when the user is using loudspeakers, a similar effect is achieved by using crosstalk cancellation to give the user the illusion that sound is coming from a particular location in space.

In some embodiments, the spatial audio is produced based on a direction and/or location of the entity with respect to the computer system or the user. In some embodiments, the spatial audio is generated such that a user of the computer system perceives audio of the audio distance indicator output as originating from a direction and/or location (e.g., direction, distance, and/or height) that corresponds to the entity with respect to the computer system or the user.

In some embodiments, the audio distance indicator output verbally indicates that the entity (e.g., a person) is detected and/or the distance to the entity.

In some embodiments, providing (706) the one or more indicators of the distance includes: providing a tactile distancing indicator output (e.g., 632, 636) (e.g., via one or more tactile output generators, and/or at a remote device in communication with the computer system, such as a watch logged into the same user account as the computer system) that changes based on the distance between the computer system and the entity.

Providing indicators, such as tactile indicators, of distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, a pitch of the tactile distance indictor output (e.g., 632, 636) changes (e.g., varies over time) based on the distance (e.g., over time) between the computer system and the entity, a frequency (e.g., characteristic frequency) of the tactile distance indictor output (e.g., 632, 636) changes based on the distance between the computer system and the entity, or (optionally, and) a waveform of the tactile distance indictor output changes based on the distance between the computer system and the entity.

In some embodiments, a pitch of the tactile distance indictor output changes (e.g., varies over time) based on the distance (e.g., over time) between the computer system and the entity.

Providing indicators, such as tactile indicators, of change in distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In accordance with some embodiments, a frequency (e.g., characteristic frequency) of the tactile distance indictor output changes based on the distance between the computer system and the entity.

Providing indicators, such as tactile indicators, of change in distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In accordance with some embodiments, a waveform of the tactile distance indictor output changes based on the distance between the computer system and the entity.

Providing indicators, such as tactile indicators, of change in distance between the computer system and the entity when a set of conditions is met for the entity provides the user with feedback about the distance to the entity, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the pitch, frequency, and waveform of the tactile distance indictor output does not change when the distance between the computer system and the entity does not change.

In some embodiments, the visual representation of the field of view of (e.g., a first camera of) the one or more cameras is displayed as part of a user interface of a computer application configured to provide (e.g., as a different feature of the computer application) variable magnification (e.g., 608), based on user input, of visual representations of a second field of view of the one or more cameras (e.g., a magnifier application that provides magnification of the second field of view, which is different from (e.g., smaller (and a subset) of) the field of view). In some embodiments, the visual representation of the field of view of the one or more cameras is configured to not be magnified based on user input (e.g., is not user zoomable).

Providing indicators of distance between the computer system and the entity when a set of conditions is met for the entity as part of a variable magnification application provides the user with quick access between magnifying nearby objects for reading and determining a distance to entities in the environment, better enabling the user of the computer system to safely navigate their environment in relation to the entity. For example, the user may want to avoid running into objects or may want to stay a healthy distance from other people to reduce the risk of infection, such as through social distancing. This feedback is particularly relevant when the user of the computer system has sight limitations. Providing improved visual feedback to the user enhances the operability of the device and makes the user-device interface more efficient (e.g., by helping the user better understand their environment, provide proper inputs, and reduce user mistakes when operating/interacting with the device) which, additionally, reduces power usage and improves battery life of the device by enabling the user to use the device more quickly and efficiently.

In some embodiments, the set of detection criteria includes a second criterion that is met when a social distancing feature is active. While the social distancing feature is not active, the computer system (e.g., 600) displays a selectable social distancing icon (e.g., 608g) (e.g., to set the social distancing feature to active). The computer system (e.g., 600) receives selection of (e.g., 650b, a tap input on) the selectable social distancing icon. In response to receiving selection of the selectable social distancing icon, the computer system (e.g., 600) sets the social distancing feature to active.

Providing the user with a mechanism to turn on or of the feature to detect and provide indicators of distance between the computer system and entities enables the computer system to avoid the extra processing of entity detection and providing user feedback when the feature is not desired, thereby reducing power usage and improving battery life.

In some embodiments, the computer system monitors for when the social distancing feature is active and does not monitor for entities when the social distancing feature is not active. In response to detecting selection of the selectable social distancing icon, the computer system optionally displays the representation of the field of view of the one or more cameras, determines whether entity(ies) in the field of view meet the set of detection criteria, and (when an entity meets the set of detection criteria) provides the one or more indicators of the distance to the user (e.g., via the displayed visual distance indicator, via the audio distance indicator output, and/or via the tactile distance indictor output). In some embodiments, prior to detecting selection of the selectable social distancing icon, the computer system does not monitor the field of view of the one or more cameras for entities (whether the first portion or any other portion) and/or does not provide the one or more indicators of distance (e.g., visual distance indicator, audio distance indicator output, and/or tactile distance indictor output) to the user about entities within the field of view.

In some embodiments, the set of detection criteria includes a third criterion that is met when a social distancing feature is active. The computer system (e.g., 600) receives one or more inputs (e.g., user inputs) that specify a respective user input (e.g., a touch gesture, a three-finger tap input, a three-finger double-tap input, a double- or triple-press of a button of the computer system) to activate the social distancing feature. Subsequent to the respective user input being specified, the computer system (e.g., 600) detects (e.g., in any of various user interface, independent of the application currently displayed, independent of the content currently displayed, and/or while displaying a field of view of one or more cameras) a user input. In response to receiving the user input: in accordance with a determination that the user input corresponds to the respective user input (e.g., 650a), the computer system (e.g., 600) activates the social distancing feature and in accordance with a determination that the user input does not correspond to the respective user input, the computer system (e.g., 600) forgoes activating the social distancing feature.

Enabling the user to define a gesture to activate monitoring of entities in the field of view of the computer system enables the computer system to activate the monitoring without the need to navigate a complex hierarchy of user interfaces. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system can receive user input to configure/specify what input will cause the computer system to start monitoring for social distancing/begin detecting for entities and/or providing the user with feedback about detected entities.

In some embodiments, the computer system (e.g., 600) receives user configuration input (e.g., selection of settings) for setting one or more parameters (e.g., 658, 660, 662) (enabling, disabling, changing characteristics of) for providing the distance between the computer system and the entity. In response to receiving the user configuration input, the computer system (e.g., 600) sets one or more parameters for providing the distance between the computer system and the entity.

In some embodiments, setting one or more parameters for providing the distance between the computer system and the entity includes: in accordance with a determination that the user configuration input corresponds to selection of a unit of length (e.g., meters, feet) (e.g., 658) of the visual distance indicator, displaying a distance using the unit of length (e.g., 618, 628) as part of displaying the visual distance indicator.

Configuring the computer system to provide desired output about distance improves the feedback provided to the user. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, setting one or more parameters for providing the distance between the computer system and the entity includes: in accordance with a determination that the user configuration input corresponds to enabling an audio indication of the distance (e.g., 662a, 662b), configuring the computer system to provide (e.g., outputting via an audio output at a speaker of the computer system and/or transmitting to wireless headphones in communication with the computer system for audio output) an audio distance indicator output (e.g., 630, 634) that changes based on the distance as part of providing the one or more indicators of the distance, and in accordance with a determination that the user configuration input corresponds to disabling the audio indication of the distance (e.g., 662a, 662b), configuring the computer system (e.g., 600) to not provide (e.g., outputting via an audio output at a speaker of the computer system and/or transmitting to wireless headphones in communication with the computer system for audio output) the audio distance indicator output that changes based on the distance as part of providing the one or more indicators of the distance.

Configuring the computer system to provide desired output about distance improves the feedback provided to the user. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the audio distance indicator output includes non-speech audio and/or speech audio, which can optionally be individually enabled or disabled via the user configuration input.

In some embodiments, setting one or more parameters for providing the distance between the computer system and the entity includes: in accordance with a determination that the user configuration input corresponds to enabling a tactile indication of the distance (e.g., 662c), configuring the computer system to provide a tactile distancing indicator output (e.g., 632, 636) (e.g., via one or more tactile output generators, and/or at a remote device in communication with the computer system, such as a watch logged into the same user account as the computer system) that changes based on the distance between the computer system and the entity as part of providing the one or more indicators of the distance; and in accordance with a determination that the user configuration input corresponds to disabling the tactile indication of the distance (e.g., 662c), configuring the computer system to not provide the tactile distancing indicator output (e.g., via one or more tactile output generators, and/or at a remote device in communication with the computer system, such as a watch logged into the same user account as the computer system) that changes based on the distance between the computer system and the entity as part of providing the one or more indicators of the distance.

Configuring the computer system to provide desired output about distance improves the feedback provided to the user. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the computer system (e.g., 600) is operating in a first detection mode, the set of detection criteria includes a center entity criterion (e.g., as in FIG. 6C) and in accordance with a determination that the computer system is operating in a second detection mod, the set of detection criteria includes a closest entity criterion that is different from the center entity criterion (e.g., as in FIG. 6E).

Operating in different modes enables the computer system to provide the user with distance information that is most relevant to the user's environment. For example, a user who is traversing an area may benefit more from information about entities that are in their path ahead of them while a user who is stationary may benefit more from information about entities both directly in front and not directly in front of them. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, when the computer system operating in the first detection mode, the set of detection criteria does not include the closest entity criterion. In some embodiments, when the computer system is operating in the second detection mode, the set of detection criteria does not include the center entity criterion.

In some embodiments, the center entity criterion is met when the entity (e.g., 624a, 624b, 624c) is determined to be in a center of the representation of the field of view (e.g., the center of the representation of the field of view overlapping at least a portion of the entity displayed as part of the representation, and/or regardless of whether an entity closer to the computer system is detected, a center portion of representation of the field of view of the one or more cameras) of the one or more cameras. In some embodiments, the center of the representation of the field of view excludes peripheral portions of the representation of the field of view. In some embodiments, the center criterion is met for an entity when the entity is the closest detected entity in the center of the representation.

In some embodiments, the center criterion is not met for entities that are not determined to be in the center of the representation of the field of view and, as a result, the computer system forgoes providing the one or more indicators of distance between the computer system and entities not in the center of the representation of the field of view.

Operating in different modes enables the computer system to provide the user with distance information that is most relevant to the user's environment. For example, a user who is traversing an area may benefit more from information about entities that are in their path ahead of them while a user who is stationary may benefit more from information about entities both directly in front and not directly in front of them. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of detection criteria includes the center entity criterion.

In some embodiments, the closest entity criterion is met when the entity (e.g., 624a, 624b, 624c) is determined to be a closest entity in the representation of the field of view of the one or more cameras to the computer system (e.g., independent of where in the field of view or the representation of the field of view the entity is located).

In some embodiments, the closest entity criterion is not met for entities that are not determined to be the closest entity (to the computer system) in the representation of the field of view and, as a result, the computer system forgoes providing the one or more indicators of distance between the computer system and those entities. In some embodiments, the computer system provides the indications of distance for only the closet entity and not for other entities.

Operating in different modes enables the computer system to provide the user with distance information that is most relevant to the user's environment. For example, a user who is traversing an area may benefit more from information about entities that are in their path ahead of them while a user who is stationary may benefit more from information about entities both directly in front and not directly in front of them. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of detection criteria includes the closest entity criterion.

In some embodiments, the computer system (e.g., 600) receives user input (e.g., on 66) to change the operating mode. In response to receiving the user input to change the operating mode: in accordance with a determination that the user input to change the operating mode corresponds to a request to operate in the first detection mode, configuring the computer system (e.g., 600) to operate in the first detection mode and in accordance with a determination that the user input to change the operating mode corresponds to a request to operate in the second detection mode, configuring the computer system (e.g., 600) to operate in the second detection mode.

Operating in different modes enables the computer system to provide the user with distance information that is most relevant to the user's environment. For example, a user who is traversing an area may benefit more from information about entities that are in their path ahead of them while a user who is stationary may benefit more from information about entities both directly in front and not directly in front of them. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system (e.g., 600) displays, via the display generation component (e.g., concurrently with the visual distance indicator, concurrently with (e.g., overlaid on) the visual representation of a field of view), a (e.g., concentric, circular) graphical element (e.g., 640) (e.g., a radar-style view, a top down view) that includes (e.g., one or more) indications (e.g., 640b-640d) of entities (e.g., all entities, all persons and not non-persons) detected in the field of view of the one or more cameras, independent of whether the entities meet the set of detection criteria, wherein the locations of the displayed indications of respective entities on the graphical element are based on a distance from the computer system to the respective entities and a direction from the computer system to the respective entities. In some embodiments, the distances among the displayed indications of respective entities on the graphical element is based on (e.g., representative of) distances among the respective entities. In some embodiments, the displayed indications of respective entities are dots or circles. In some embodiments, the graphical element includes a location (e.g., identified by a visual marker, and/or a center of the graphical element) corresponding to the computer system and distances between the location corresponding to the computer system and the indications of respective entities are based on (e.g., are proportional to) determined distances between the computer system and the respective entities.

Providing a radar-style view that includes visual representations of multiple (e.g., all) detected entities enables the computer system to provide the user with a more comprehensive view of the user's environment. For example, a user who wants to traverse an area may benefit from information about the location of multiple entities in the area. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, a selectable option is displayed which, when activated, causes display of the graphical element that includes indications of entities detected in the field of view.

In some embodiments, the computer system (e.g., 600) receives selection of (e.g., 650e, tap on) the graphical element (e.g., 640) that includes (e.g., one or more) indications of entities. In response to receiving selection of the graphical element that includes indications of entities, the computer system (e.g., 600) enlarges the graphical element (e.g., 640) and displays the enlarged graphical element overlaid on the representation of the field of view (as shown in FIG. 6J).

Providing an enlarged radar-style view that includes visual representations of multiple (e.g., all) detected entities enables the computer system to provide the user with a more easily visually understandable view of the user's environment. For example, a user who wants to traverse an area may benefit from information about the location of multiple entities in the area. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a failure to determine that an entity meets the set of detection criteria (e.g., as in FIGS. 6D and 6H) (e.g., a determination that no entity is detected that meets the set of detection criteria), the computer system (e.g., 600) displays, via the display generation component (e.g., concurrently with the visual representation of the field of view of the one or more cameras), an indication (e.g., 620, 622c) that no entity meets the set of detection criteria (e.g., display "No persons found").

Providing an indication that no entities meet the detection criteria provides the user with feedback about the user's surroundings. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of detection criteria includes a maximum distance criterion that is met when the entity is within a threshold distance from the computer system (e.g., within 15 feet from the computer system). Thus, in some embodiments, persons that are more than the threshold distance from the computer system do not meet the detection criteria and a distance for the person is not displayed.

Limiting the feedback to entities that are within a threshold distance from the computer system provides the user with feedback about the user's more immediate surroundings. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the visual distance indicator (e.g., 616, 626) is displayed overlaid on the representation of the field of view and the visual distance indicator includes a linear object (e.g., a line, a solid line, a dotted line) that includes an endpoint (e.g., 616b, 626b) that is adjacent to (or overlaid on) the entity (e.g., to the person, to the feet of the person) displayed in the representation of the field of view.

Providing a linear object (e.g., a line) that extends to the entity provides the user with feedback about which entity in the field of view provided distance information corresponds to. This is particularly helpful for the user when multiple entities are displayed in the representation of the field of view, but distances are provided for only a subset (e.g., one) of the entities. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, a second endpoint of the linear object is adjacent to a numerical representation of the distance between the computer system to the entity.

In some embodiments, the visual representation 612, 624) of the field of view of the one or more cameras includes an indicator (e.g., 610b) that indicates that the computer system is currently configured to display the visual distance indicator that indicates the distance between the computer system and the entity in accordance with a determination that the entity meets a set of detection criteria. In some embodiments, the computer system (e.g., 600) displays a second visual representation of the field of view of the one or more cameras that: in accordance with a determination that the computer system, while displaying the second visual representation of the field of view of the one or more cameras, is currently configured to display the visual distance indicator that indicates the distance between the computer system and the entity in accordance with a determination that the entity meets a set of detection criteria, includes the indicator (e.g., 610b) that indicates that the computer system is currently configured to display the visual distance indicator that indicates the distance between the computer system and the entity in accordance with a determination that the entity meets a set of detection criteria; and in accordance with a determination that the computer system, while displaying the second visual representation of the field of view of the one or more cameras, is not currently configured to display the visual distance indicator that indicates the distance between the computer system and the entity in accordance with a determination that the entity meets a set of detection criteria, does not include the indicator that indicates that the computer system is currently configured to display the visual distance indicator that indicates the distance between the computer system and the entity in accordance with a determination that the entity meets a set of detection criteria.

In some embodiments, while displaying the representation of the field of view, displaying, via the display generation component, an indication overlaid on the field of view that indicates a social distancing feature (e.g., the computer system is monitoring the field of view of the one or more camera for entities that meet the set of one or more criteria) is activated to detect entities in the field of view.

Providing the user with a visual indication that the social distancing feature is activated provides the user with feedback about the state of the computer system and whether the computer system will provide alerts/distances as entities come near. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system provides the user with visual feedback that the computer system is monitoring for social distancing and/or attempting to detect entities to provide distance feedback for entities that meet the set of distance criteria.

In some embodiments, while displaying the representation of the field of view and monitoring the field of view of the one or more camera for entities that meet the set of one or more criteria: the computer system (e.g., 600) displays, via the display generation component, a toggle (e.g., 608g, 644) (or button). The computer system (e.g., 600) receives selection (e.g., 650f) of the toggle. In response to receiving selection of the toggle (and in accordance with a determination that the computer system was monitoring the field of view of the one or more camera for entities that meet the set of one or more criteria when selection of the toggle was received), the computer system (e.g., 600) ceases monitoring the field of view of the one or more camera for entities that meet the set of one or more criteria.

Ceasing monitoring of the field of view for entities in response to user input provides the user with a mechanism to reduce processing when entity detection is not required, thereby reducing power usage and improving the battery life of the device.

In some embodiments, in response to receiving selection of the toggle, and in accordance with a determination that the computer system was not monitoring the field of view of the one or more camera for entities that meet the set of one or more criteria when selection of the toggle was received, initiating monitoring of the field of view of the one or more camera for entities that meet the set of one or more criteria.

In accordance with some embodiments, the set of detection criteria includes a person detection criterion that is met when the entity is (e.g., determined to be) a person (e.g., not an animal, and/or not a non-person such as an object). In accordance with some embodiments, the set of detection criteria alternatively includes an object detection criterion that is met when the entity is (e.g., determined to be) an object (e.g., not a person).

As described below, method 700 provides an intuitive way for providing an indication of distance to an entity. The method reduces the cognitive burden on a user for determining distances to entities, thereby creating a more efficient human-machine interface. For battery-operated computing devices, enabling a user to determine distances to entities faster and more efficiently conserves power and increases the time between battery charges.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to provide a user with an estimate of distance between the user and an entity located within a surrounding of the user. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to determine information related to the surroundings of the user, such as entities that may be located within proximity to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of location services and entity detection, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, an estimated distance between an electronic device and an entity within a field of view of a camera of the electronic device may be determined and conveyed to a user without using location information associated with the electronic device.

What is claimed is:

1. A computer system, comprising:
   one or more cameras;
   a display generation component;
   one or more processors; and
   memory storing one or more programs configured to be executed by the one or more processors, the one or more programs including instructions for:
      displaying, via the display generation component, a visual representation of a field of view of the one or more cameras;
      in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes:
         displaying, via the display generation component, a visual distance indicator that indicates a distance between the computer system and the entity; and
         providing a tactile distancing indicator output that changes based on the distance between the computer system and the entity, wherein a pitch of the tactile distancing indicator output changes based on the distance between the computer system and the entity, a frequency of the tactile distancing indicator output changes based on the distance between the computer system and the entity, or a waveform of the tactile distancing indicator output changes based on the distance between the computer system and the entity; and
      in accordance with a failure to determine that an entity meets the set of detection criteria, forgoing providing the one or more indicators of the distance between the computer system and the entity.

2. The computer system of claim 1, wherein providing the one or more indicators of the distance includes providing an audio distance indicator output that changes based on the distance between the computer system and the entity and wherein a pitch of the audio distance indicator output becomes higher as the distance between the computer system and the entity decreases, a frequency of the audio distance indicator output becomes higher as the distance between the computer system and the entity decreases, or a volume of the audio distance indicator output increases as the distance between the computer system and the entity decreases.

3. The computer system of claim 1, wherein providing the one or more indicators of the distance includes providing an audio distance indicator output that changes based on the distance between the computer system and the entity and wherein the audio distance indicator output includes stereo components, the stereo components including a first audio channel with a first characteristic and a second audio channel with a second characteristic that is different from the first characteristic, the first characteristic and the second characteristic based on the distance between the computer system and the entity.

4. The computer system of claim 1, wherein the visual representation of the field of view of the one or more cameras is displayed as part of a user interface of a computer application configured to provide variable magnification, based on user input, of visual representations of a second field of view of the one or more cameras.

5. The computer system of claim 1, wherein the set of detection criteria includes a second criterion that is met when a social distancing feature is active, and wherein the one or more programs further include instructions for:
   while the social distancing feature is not active, displaying a selectable social distancing icon;
   receiving selection of the selectable social distancing icon; and
   in response to receiving selection of the selectable social distancing icon, setting the social distancing feature to active.

6. The computer system of claim 1, wherein the set of detection criteria includes a third criterion that is met when a social distancing feature is active, and wherein the one or more programs further include instructions for:
   receiving one or more inputs that specify a respective user input to activate the social distancing feature; and
   subsequent to the respective user input being specified, detecting a user input;
   in response to receiving the user input:
      in accordance with a determination that the user input corresponds to the respective user input, activating the social distancing feature; and in accordance with a determination that the user input does not correspond to the respective user input, forgoing activating the social distancing feature.

7. The computer system of claim 1, wherein the one or more programs further include instructions for:
receiving user configuration input for setting one or more parameters for providing the distance between the computer system and the entity; and
in response to receiving the user configuration input, setting one or more parameters for providing the distance between the computer system and the entity.

8. The computer system of claim 7, wherein setting one or more parameters for providing the distance between the computer system and the entity includes:
in accordance with a determination that the user configuration input corresponds to selection of a unit of length of the visual distance indicator, displaying a distance using the unit of length as part of displaying the visual distance indicator.

9. The computer system of claim 7, wherein setting one or more parameters for providing the distance between the computer system and the entity includes:
in accordance with a determination that the user configuration input corresponds to enabling an audio indication of the distance, configuring the computer system to provide an audio distance indicator output that changes based on the distance as part of providing the one or more indicators of the distance; and
in accordance with a determination that the user configuration input corresponds to disabling the audio indication of the distance, configuring the computer system to not provide the audio distance indicator output that changes based on the distance as part of providing the one or more indicators of the distance.

10. The computer system of claim 7, wherein setting one or more parameters for providing the distance between the computer system and the entity includes:
in accordance with a determination that the user configuration input corresponds to enabling a tactile indication of the distance, configuring the computer system to provide the tactile distancing indicator output that changes based on the distance between the computer system and the entity as part of providing the one or more indicators of the distance; and
in accordance with a determination that the user configuration input corresponds to disabling the tactile indication of the distance, configuring the computer system to not provide the tactile distancing indicator output that changes based on the distance between the computer system and the entity as part of providing the one or more indicators of the distance.

11. The computer system of claim 1, wherein:
in accordance with a determination that the computer system is operating in a first detection mode, the set of detection criteria includes a center entity criterion; and
in accordance with a determination that the computer system is operating in a second detection mode, the set of detection criteria includes a closest entity criterion that is different from the center entity criterion.

12. The computer system of claim 11, wherein the center entity criterion is met when the entity is determined to be in a center of the representation of the field of view of the one or more cameras.

13. The computer system of claim 11, wherein the closest entity criterion is met when the entity is determined to be a closest entity in the representation of the field of view of the one or more cameras to the computer system.

14. The computer system of claim 11, wherein the one or more programs further include instructions for:
receiving user input to change an operating mode; and
in response to receiving the user input to change the operating mode:
in accordance with a determination that the user input to change the operating mode corresponds to a request to operate in the first detection mode, configuring the computer system to operate in the first detection mode; and
in accordance with a determination that the user input to change the operating mode corresponds to a request to operate in the second detection mode, configuring the computer system to operate in the second detection mode.

15. The computer system of claim 1, wherein the one or more programs further include instructions for:
displaying, via the display generation component, a graphical element that includes indications of entities detected in the field of view of the one or more cameras, independent of whether the entities meet the set of detection criteria, wherein the locations of the displayed indications of respective entities on the graphical element are based on a distance from the computer system to the respective entities and a direction from the computer system to the respective entities;
receiving selection of the graphical element that includes indications of entities; and
in response to receiving selection of the graphical element that includes indications of entities, enlarging the graphical element and displaying the enlarged graphical element overlaid on the representation of the field of view.

16. The computer system of claim 1, wherein the visual distance indicator is displayed overlaid on the representation of the field of view and the visual distance indicator includes a linear object that includes an endpoint that is adjacent to the entity displayed in the representation of the field of view.

17. The computer system of claim 1, wherein the visual representation of the field of view of the one or more cameras includes an indicator that indicates that the computer system is currently configured to display the visual distance indicator that indicates the distance between the computer system and the entity in accordance with a determination that the entity meets a set of detection criteria, and wherein the one or more programs further include instructions for:
displaying a second visual representation of the field of view of the one or more cameras that:
in accordance with a determination that the computer system, while displaying the second visual representation of the field of view of the one or more cameras, is currently configured to display the visual distance indicator that indicates the distance between the computer system and the entity in accordance with a determination that the entity meets a set of detection criteria, includes the indicator that indicates that the computer system is currently configured to display the visual distance indicator that indicates the distance between the computer system and the entity in accordance with a determination that the entity meets a set of detection criteria; and
in accordance with a determination that the computer system, while displaying the second visual representation of the field of view of the one or more cameras, is not currently configured to display the visual distance indicator that indicates the distance between the computer system and the entity in accordance with a determination that the entity meets a set of detection criteria, does not include the indicator that indicates that the computer system is currently configured to display the visual distance indicator that indicates the distance between the computer system and the entity in accordance with a determination that the entity meets a set of detection criteria.

18. The computer system of claim 1, wherein the one or more programs further include instructions for:
While displaying the representation of the field of view and monitoring the field of view of the one or more camera for entities that meet a set of one or more criteria:
displaying, via the display generation component, a toggle; and
receiving selection of the toggle; and
in response to receiving selection of the toggle, ceasing monitoring the field of view of the one or more camera for entities that meet the set of one or more criteria.

19. A non-transitory computer-readable storage medium storing one or more programs configured to be executed by one or more processors of a computer system that is in communication with one or more cameras and a display generation component, the one or more programs including instructions for:
displaying, via the display generation component, a visual representation of a field of view of the one or more cameras;
in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes:
displaying, via the display generation component, a visual distance indicator that indicates a distance between the computer system and the entity; and
providing a tactile distancing indicator output that changes based on the distance between the computer system and the entity, wherein a pitch of the tactile distancing indicator output changes based on the distance between the computer system and the entity, a frequency of the tactile distancing indicator output changes based on the distance between the computer system and the entity, or a waveform of the tactile distancing indicator output changes based on the distance between the computer system and the entity; and
in accordance with a failure to determine that an entity meets the set of detection criteria, forgoing providing the one or more indicators of the distance between the computer system and the entity.

20. The non-transitory computer-readable storage medium of claim 19, wherein providing the one or more indicators of the distance includes providing an audio distance indicator output that changes based on the distance between the computer system and the entity and wherein a pitch of the audio distance indicator output becomes higher as the distance between the computer system and the entity decreases, a frequency of the audio distance indicator output becomes higher as the distance between the computer system and the entity decreases, or a volume of the audio distance indicator output increases as the distance between the computer system and the entity decreases.

21. The non-transitory computer-readable storage medium of claim 19, wherein providing the one or more indicators of the distance includes providing an audio distance indicator output that changes based on the distance between the computer system and the entity and wherein the audio distance indicator output includes stereo components, the stereo components including a first audio channel with a first characteristic and a second audio channel with a second characteristic that is different from the first characteristic, the first characteristic and the second characteristic based on the distance between the computer system and the entity.

22. The non-transitory computer-readable storage medium of claim 19, wherein the visual representation of the field of view of the one or more cameras is displayed as part of a user interface of a computer application configured to provide variable magnification, based on user input, of visual representations of a second field of view of the one or more cameras.

23. The non-transitory computer-readable storage medium of claim 19, wherein the set of detection criteria includes a second criterion that is met when a social distancing feature is active, and wherein the one or more programs further include instructions for:
while the social distancing feature is not active, displaying a selectable social distancing icon;
receiving selection of the selectable social distancing icon; and
in response to receiving selection of the selectable social distancing icon, setting the social distancing feature to active.

24. The non-transitory computer-readable storage medium of claim 19, wherein the set of detection criteria includes a third criterion that is met when a social distancing feature is active, and wherein the one or more programs further include instructions for:
receiving one or more inputs that specify a respective user input to activate the social distancing feature; and
subsequent to the respective user input being specified, detecting a user input;
in response to receiving the user input:
in accordance with a determination that the user input corresponds to the respective user input, activating the social distancing feature; and
in accordance with a determination that the user input does not correspond to the respective user input, forgoing activating the social distancing feature.

25. The non-transitory computer-readable storage medium of claim 19, wherein the one or more programs further include instructions for:
receiving user configuration input for setting one or more parameters for providing the distance between the computer system and the entity; and
in response to receiving the user configuration input, setting one or more parameters for providing the distance between the computer system and the entity.

26. The non-transitory computer-readable storage medium of claim 25, wherein setting one or more parameters for providing the distance between the computer system and the entity includes:
in accordance with a determination that the user configuration input corresponds to selection of a unit of length of the visual distance indicator, displaying a distance using the unit of length as part of displaying the visual distance indicator.

27. The non-transitory computer-readable storage medium of claim 25, wherein setting one or more parameters for providing the distance between the computer system and the entity includes:
- in accordance with a determination that the user configuration input corresponds to enabling an audio indication of the distance, configuring the computer system to provide an audio distance indicator output that changes based on the distance as part of providing the one or more indicators of the distance; and
- in accordance with a determination that the user configuration input corresponds to disabling the audio indication of the distance, configuring the computer system to not provide the audio distance indicator output that changes based on the distance as part of providing the one or more indicators of the distance.

28. The non-transitory computer-readable storage medium of claim 25, wherein setting one or more parameters for providing the distance between the computer system and the entity includes:
- in accordance with a determination that the user configuration input corresponds to enabling a tactile indication of the distance, configuring the computer system to provide the tactile distancing indicator output that changes based on the distance between the computer system and the entity as part of providing the one or more indicators of the distance; and
- in accordance with a determination that the user configuration input corresponds to disabling the tactile indication of the distance, configuring the computer system to not provide the tactile distancing indicator output that changes based on the distance between the computer system and the entity as part of providing the one or more indicators of the distance.

29. The non-transitory computer-readable storage medium of claim 19, wherein:
- in accordance with a determination that the computer system is operating in a first detection mode, the set of detection criteria includes a center entity criterion; and
- in accordance with a determination that the computer system is operating in a second detection mode, the set of detection criteria includes a closest entity criterion that is different from the center entity criterion.

30. The non-transitory computer-readable storage medium of claim 29, wherein the center entity criterion is met when the entity is determined to be in a center of the representation of the field of view of the one or more cameras.

31. The non-transitory computer-readable storage medium of claim 29, wherein the closest entity criterion is met when the entity is determined to be a closest entity in the representation of the field of view of the one or more cameras to the computer system.

32. The non-transitory computer-readable storage medium of claim 29, wherein the one or more programs further include instructions for:
- receiving user input to change an operating mode; and
- in response to receiving the user input to change the operating mode:
  - in accordance with a determination that the user input to change the operating mode corresponds to a request to operate in the first detection mode, configuring the computer system to operate in the first detection mode; and
  - in accordance with a determination that the user input to change the operating mode corresponds to a request to operate in the second detection mode, configuring the computer system to operate in the second detection mode.

33. The non-transitory computer-readable storage medium of claim 19, wherein the one or more programs further include instructions for:
- displaying, via the display generation component, a graphical element that includes indications of entities detected in the field of view of the one or more cameras, independent of whether the entities meet the set of detection criteria, wherein the locations of the displayed indications of respective entities on the graphical element are based on a distance from the computer system to the respective entities and a direction from the computer system to the respective entities;
- receiving selection of the graphical element that includes indications of entities; and
- in response to receiving selection of the graphical element that includes indications of entities, enlarging the graphical element and displaying the enlarged graphical element overlaid on the representation of the field of view.

34. The non-transitory computer-readable storage medium of claim 19, wherein the visual distance indicator is displayed overlaid on the representation of the field of view and the visual distance indicator includes a linear object that includes an endpoint that is adjacent to the entity displayed in the representation of the field of view.

35. The non-transitory computer-readable storage medium of claim 19, wherein the visual representation of the field of view of the one or more cameras includes an indicator that indicates that the computer system is currently configured to display the visual distance indicator that indicates the distance between the computer system and the entity in accordance with a determination that the entity meets a set of detection criteria, and wherein the one or more programs further include instructions for:
- displaying a second visual representation of the field of view of the one or more cameras that:
  - in accordance with a determination that the computer system, while displaying the second visual representation of the field of view of the one or more cameras, is currently configured to display the visual distance indicator that indicates the distance between the computer system and the entity in accordance with a determination that the entity meets a set of detection criteria, includes the indicator that indicates that the computer system is currently configured to display the visual distance indicator that indicates the distance between the computer system and the entity in accordance with a determination that the entity meets a set of detection criteria; and
  - in accordance with a determination that the computer system, while displaying the second visual representation of the field of view of the one or more cameras, is not currently configured to display the visual distance indicator that indicates the distance between the computer system and the entity in accordance with a determination that the entity meets a set of detection criteria, does not include the indicator that indicates that the computer system is currently configured to display the visual distance indicator that indicates the distance between the computer system and the entity in accordance with a determination that the entity meets a set of detection criteria.

36. The non-transitory computer-readable storage medium of claim 19, wherein the one or more programs further include instructions for:
- while displaying the representation of the field of view and monitoring the field of view of the one or more camera for entities that meet a set of one or more criteria:
  - displaying, via the display generation component, a toggle; and
  - receiving selection of the toggle; and
- in response to receiving selection of the toggle, ceasing monitoring the field of view of the one or more camera for entities that meet the set of one or more criteria.

37. A method, comprising:
- at a computer system that is in communication with one or more cameras and a display generation component:
  - displaying, via the display generation component, a visual representation of a field of view of the one or more cameras;
  - in accordance with a determination that an entity meets a set of detection criteria, the set of detection criteria including a first criterion that is met when the entity is detected within the field of view of the one or more cameras, providing, concurrently with the visual representation of the field of view that includes the entity, one or more indicators of distance between the computer system and the entity, wherein providing the one or more indicators of distance includes:
    - displaying, via the display generation component, a visual distance indicator that indicates a distance between the computer system and the entity; and
    - providing a tactile distancing indicator output that changes based on the distance between the computer system and the entity, wherein a pitch of the tactile distancing indicator output changes based on the distance between the computer system and the entity, a frequency of the tactile distancing indicator output changes based on the distance between the computer system and the entity, or a waveform of the tactile distancing indicator output changes based on the distance between the computer system and the entity; and
  - in accordance with a failure to determine that an entity meets the set of detection criteria, forgoing providing the one or more indicators of the distance between the computer system and the entity.

38. The method of claim 37, wherein providing the one or more indicators of the distance includes providing an audio distance indicator output that changes based on the distance between the computer system and the entity and wherein a pitch of the audio distance indicator output becomes higher as the distance between the computer system and the entity decreases, a frequency of the audio distance indicator output becomes higher as the distance between the computer system and the entity decreases, or a volume of the audio distance indicator output increases as the distance between the computer system and the entity decreases.

39. The method of claim 37, wherein providing the one or more indicators of the distance includes providing an audio distance indicator output that changes based on the distance between the computer system and the entity and wherein the audio distance indicator output includes stereo components, the stereo components including a first audio channel with a first characteristic and a second audio channel with a second characteristic that is different from the first characteristic, the first characteristic and the second characteristic based on the distance between the computer system and the entity.

40. The method of claim 37, wherein the visual representation of the field of view of the one or more cameras is displayed as part of a user interface of a computer application configured to provide variable magnification, based on user input, of visual representations of a second field of view of the one or more cameras.

41. The method of claim 37, wherein the set of detection criteria includes a second criterion that is met when a social distancing feature is active, the method further comprising:
- while the social distancing feature is not active, displaying a selectable social distancing icon;
- receiving selection of the selectable social distancing icon; and
- in response to receiving selection of the selectable social distancing icon, setting the social distancing feature to active.

42. The method of claim 37, wherein the set of detection criteria includes a third criterion that is met when a social distancing feature is active, the method further comprising:
- receiving one or more inputs that specify a respective user input to activate the social distancing feature; and
- subsequent to the respective user input being specified, detecting a user input;
- in response to receiving the user input:
  - in accordance with a determination that the user input corresponds to the respective user input, activating the social distancing feature; and
  - in accordance with a determination that the user input does not correspond to the respective user input, forgoing activating the social distancing feature.

43. The method of claim 37, further comprising:
- receiving user configuration input for setting one or more parameters for providing the distance between the computer system and the entity; and
- in response to receiving the user configuration input, setting one or more parameters for providing the distance between the computer system and the entity.

44. The method of claim 43, wherein setting one or more parameters for providing the distance between the computer system and the entity includes:
- in accordance with a determination that the user configuration input corresponds to selection of a unit of length of the visual distance indicator, displaying a distance using the unit of length as part of displaying the visual distance indicator.

45. The method of claim 43, wherein setting one or more parameters for providing the distance between the computer system and the entity includes:
- in accordance with a determination that the user configuration input corresponds to enabling an audio indication of the distance, configuring the computer system to provide an audio distance indicator output that changes based on the distance as part of providing the one or more indicators of the distance; and
- in accordance with a determination that the user configuration input corresponds to disabling the audio indication of the distance, configuring the computer system to not provide the audio distance indicator output that changes based on the distance as part of providing the one or more indicators of the distance.

46. The method of claim 43, wherein setting one or more parameters for providing the distance between the computer system and the entity includes:
- in accordance with a determination that the user configuration input corresponds to enabling a tactile indication of the distance, configuring the computer system to provide the tactile distancing indicator output that changes based on the distance between the computer system and the entity as part of providing the one or more indicators of the distance; and in accordance with a determination that the user configuration input corresponds to disabling the tactile indication of the distance, configuring the computer system to not provide the tactile distancing indicator output that changes based on the distance between the computer system and the entity as part of providing the one or more indicators of the distance.

47. The method of claim 37, wherein:
in accordance with a determination that the computer system is operating in a first detection mode, the set of detection criteria includes a center entity criterion; and
in accordance with a determination that the computer system is operating in a second detection mode, the set of detection criteria includes a closest entity criterion that is different from the center entity criterion.

48. The method of claim 47, wherein the center entity criterion is met when the entity is determined to be in a center of the representation of the field of view of the one or more cameras.

49. The method of claim 47, wherein the closest entity criterion is met when the entity is determined to be a closest entity in the representation of the field of view of the one or more cameras to the computer system.

50. The method of claim 47, further comprising:
receiving user input to change an operating mode; and
in response to receiving the user input to change the operating mode:
in accordance with a determination that the user input to change the operating mode corresponds to a request to operate in the first detection mode, configuring the computer system to operate in the first detection mode; and
in accordance with a determination that the user input to change the operating mode corresponds to a request to operate in the second detection mode, configuring the computer system to operate in the second detection mode.

51. The method of claim 37, further comprising:
displaying, via the display generation component, a graphical element that includes indications of entities detected in the field of view of the one or more cameras, independent of whether the entities meet the set of detection criteria, wherein the locations of the displayed indications of respective entities on the graphical element are based on a distance from the computer system to the respective entities and a direction from the computer system to the respective entities;
receiving selection of the graphical element that includes indications of entities; and
in response to receiving selection of the graphical element that includes indications of entities, enlarging the graphical element and displaying the enlarged graphical element overlaid on the representation of the field of view.

52. The method of claim 37, wherein the visual distance indicator is displayed overlaid on the representation of the field of view and the visual distance indicator includes a linear object that includes an endpoint that is adjacent to the entity displayed in the representation of the field of view.

53. The method of claim 37, wherein the visual representation of the field of view of the one or more cameras includes an indicator that indicates that the computer system is currently configured to display the visual distance indicator that indicates the distance between the computer system and the entity in accordance with a determination that the entity meets a set of detection criteria, the method further comprising:
displaying a second visual representation of the field of view of the one or more cameras that:
in accordance with a determination that the computer system, while displaying the second visual representation of the field of view of the one or more cameras, is currently configured to display the visual distance indicator that indicates the distance between the computer system and the entity in accordance with a determination that the entity meets a set of detection criteria, includes the indicator that indicates that the computer system is currently configured to display the visual distance indicator that indicates the distance between the computer system and the entity in accordance with a determination that the entity meets a set of detection criteria; and
in accordance with a determination that the computer system, while displaying the second visual representation of the field of view of the one or more cameras, is not currently configured to display the visual distance indicator that indicates the distance between the computer system and the entity in accordance with a determination that the entity meets a set of detection criteria, does not include the indicator that indicates that the computer system is currently configured to display the visual distance indicator that indicates the distance between the computer system and the entity in accordance with a determination that the entity meets a set of detection criteria.

54. The method of claim 37, further comprising:
While displaying the representation of the field of view and monitoring the field of view of the one or more camera for entities that meet a set of one or more criteria:
displaying, via the display generation component, a toggle; and
receiving selection of the toggle; and
in response to receiving selection of the toggle, ceasing monitoring the field of view of the one or more camera for entities that meet the set of one or more criteria.

* * * * *